US012484917B2

(12) United States Patent
Dayton et al.

(10) Patent No.: US 12,484,917 B2
(45) Date of Patent: Dec. 2, 2025

(54) FIRST METATARSAL LATERAL RELEASE INSTRUMENT AND TECHNIQUE

(71) Applicant: Treace Medical Concepts, Inc., Ponte Vedra, FL (US)

(72) Inventors: Paul Dayton, Ankeny, IA (US); William T. DeCarbo, Pittsburgh, PA (US); Daniel J. Hatch, Greeley, CO (US); Jody McAleer, Jefferson City, MO (US); Robert D. Santrock, Morgantown, WV (US); W. Bret Smith, Durango, CO (US); Mark Erik Easley, Durham, NC (US); Bryan Wilcox, St. Augustine, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 332 days.

(21) Appl. No.: 18/173,634

(22) Filed: Feb. 23, 2023

(65) Prior Publication Data

US 2023/0263543 A1 Aug. 24, 2023

Related U.S. Application Data

(60) Provisional application No. 63/313,131, filed on Feb. 23, 2022.

(51) Int. Cl.
*A61B 17/17* (2006.01)
*A61B 17/16* (2006.01)
*A61B 17/56* (2006.01)

(52) U.S. Cl.
CPC ...... *A61B 17/1775* (2016.11); *A61B 17/1682* (2013.01); *A61B 2017/564* (2013.01)

(58) Field of Classification Search
CPC ............ A61B 17/1775; A61B 17/1682; A61B 2017/564
See application file for complete search history.

(56) References Cited

U.S. PATENT DOCUMENTS

D175,170 S 7/1955 Johnson
3,664,022 A 5/1972 Small
(Continued)

FOREIGN PATENT DOCUMENTS

AU 2009227957 B2 7/2014
CA 2491824 A1 9/2005
(Continued)

OTHER PUBLICATIONS

Dual-Point Seam Ripper Turning Kit, rockier.com, first reviewed Jan. 30, 2017 [online], [site visited Mar. 19, 2024], Available from internet, URL: https://www.rockler.com/dual-point-seam-ripper-turning-kit (Year: 2017).

(Continued)

*Primary Examiner* — Zade Coley
*Assistant Examiner* — Diana Jones
(74) *Attorney, Agent, or Firm* — Fredrikson & Byron, P.A.

(57) ABSTRACT

Instruments and techniques can be used to release a first metatarsal for realignment. In some implementations, a techniques involves surgically accessing a sesamoidal ligament in a foot of a patient and advancing a guiding projection of a cutting instrument under the sesamoidal ligament. This can capture the sesamoidal ligament between the guiding projection of the cutting instrument and a cutting surface of the cutting instrument that is recessed relative to a distal end of the guiding projection. The techniques further involves cutting the sesamoidal ligament with the cutting surface of the cutting instrument.

24 Claims, 12 Drawing Sheets

(56) References Cited

U.S. PATENT DOCUMENTS 4,069,824 A 1/1978 Weinstock
4,159,716 A 7/1979 Borchers
4,187,840 A 2/1980 Watanabe
4,335,715 A 6/1982 Kirkley
4,338,927 A 7/1982 Volkov et al.
4,349,018 A 9/1982 Chambers
D268,073 S 3/1983 Schaeffer
4,409,973 A 10/1983 Neufeld
4,440,168 A 4/1984 Warren
4,501,268 A 2/1985 Comparetto
4,502,474 A 3/1985 Comparetto
4,509,511 A 4/1985 Neufeld
D279,603 S 7/1985 Thorsbakken
4,565,191 A 1/1986 Slocum
4,570,624 A 2/1986 Wu
4,627,425 A 12/1986 Reese
4,628,919 A 12/1986 Clyburn
4,632,102 A 12/1986 Comparetto
4,664,102 A 5/1987 Comparetto
4,708,133 A 11/1987 Comparetto
4,736,737 A 4/1988 Fargie et al.
4,750,481 A 6/1988 Reese
4,754,746 A 7/1988 Cox
4,757,810 A 7/1988 Reese
4,895,141 A 1/1990 Koeneman et al.
4,952,214 A 8/1990 Comparetto
4,959,066 A 9/1990 Dunn et al.
4,978,347 A 12/1990 Ilizarov
4,988,349 A 1/1991 Pennig
4,995,875 A 2/1991 Coes
5,021,056 A 6/1991 Hofmann et al.
5,035,698 A 7/1991 Comparetto
D318,996 S 8/1991 Israelson
5,042,983 A 8/1991 Rayhack
5,049,149 A 9/1991 Schmidt
5,053,039 A 10/1991 Hofmann et al.
5,078,719 A 1/1992 Schreiber
5,112,334 A 5/1992 Alchermes et al.
5,147,364 A 9/1992 Comparetto
5,176,685 A 1/1993 Rayhack
5,207,676 A 5/1993 Canadell et al.
D336,413 S 6/1993 Ebert
5,246,444 A 9/1993 Schreiber
5,254,115 A 10/1993 Bhatta et al.
5,254,119 A 10/1993 Schreiber
5,312,412 A 5/1994 Whipple
5,358,504 A 10/1994 Paley et al.
5,364,402 A 11/1994 Mumme et al.
5,374,271 A 12/1994 Hwang
5,413,579 A 5/1995 Du Toit
5,417,694 A 5/1995 Marik et al.
5,449,360 A 9/1995 Schreiber
5,470,335 A 11/1995 Du Toit
5,490,854 A 2/1996 Fisher et al.
5,529,075 A 6/1996 Clark
5,540,695 A 7/1996 Levy
5,578,038 A 11/1996 Slocum
D377,093 S 12/1996 Michelson
5,586,564 A 12/1996 Barrett et al.
5,601,565 A 2/1997 Huebner
5,613,969 A 3/1997 Jenkins, Jr.
5,620,442 A 4/1997 Bailey et al.
5,620,448 A 4/1997 Puddu
5,643,270 A 7/1997 Combs
D383,663 S 9/1997 Gray et al.
5,667,510 A 9/1997 Combs
H1706 H 1/1998 Mason
5,722,978 A 3/1998 Jenkins
5,749,875 A 5/1998 Puddu
5,779,709 A 7/1998 Harris et al.
5,788,695 A 8/1998 Richardson
5,803,924 A 9/1998 Oni et al.
5,810,822 A 9/1998 Mortier
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Viegas et al.
5,951,556 A 9/1999 Faccioli et al.
5,980,526 A 11/1999 Johnson et al.
5,984,931 A 11/1999 Greenfield
6,007,535 A 12/1999 Rayhack et al.
6,027,504 A 2/2000 Mcguire
6,030,391 A 2/2000 Brainard et al.
6,162,223 A 12/2000 Orsak et al.
6,171,309 B1 1/2001 Huebner
6,203,545 B1 3/2001 Stoffella
6,248,109 B1 6/2001 Stoffella
6,391,031 B1 5/2002 Toomey
6,416,465 B2 7/2002 Brau
6,478,799 B1 11/2002 Williamson
6,511,481 B2 1/2003 von Hoffmann et al.
6,547,793 B1 4/2003 McGuire
6,676,662 B1 1/2004 Bagga et al.
6,719,773 B1 4/2004 Boucher et al.
6,743,233 B1 6/2004 Baldwin et al.
6,755,838 B2 6/2004 Trnka
6,796,986 B2 9/2004 Duffner
6,859,661 B2 2/2005 Tuke
6,964,645 B1 11/2005 Smits
7,018,383 B2 3/2006 McGuire
7,033,361 B2 4/2006 Collazo
7,097,647 B2 8/2006 Segler et al.
7,112,204 B2 9/2006 Justin et al.
7,153,310 B2 12/2006 Ralph et al.
7,182,766 B1 2/2007 Mogul
D546,948 S 7/2007 Huttner
7,241,298 B2 7/2007 Nemec et al.
7,282,054 B2 10/2007 Steffensmeier et al.
7,377,924 B2 5/2008 Raistrick et al.
7,465,303 B2 12/2008 Riccione et al.
7,540,874 B2 6/2009 Trumble et al.
7,572,258 B2 8/2009 Stiernborg
7,641,660 B2 1/2010 Lakin et al.
D610,257 S 2/2010 Horton
7,686,811 B2 3/2010 Byrd et al.
7,691,108 B2 4/2010 Lavallee
7,763,026 B2 7/2010 Egger et al.
D629,900 S 12/2010 Fisher
7,967,823 B2 6/2011 Ammann et al.
7,972,338 B2 7/2011 O'Brien
D646,389 S 10/2011 Claypool et al.
8,057,478 B2 11/2011 Kuczynski et al.
8,062,301 B2 11/2011 Ammann et al.
D651,315 S 12/2011 Bertoni et al.
D651,316 S 12/2011 May et al.
8,080,010 B2 12/2011 Schulz et al.
8,080,045 B2 12/2011 Wotton, III
8,083,746 B2 12/2011 Novak
8,123,753 B2 2/2012 Poncet
8,137,406 B2 3/2012 Novak et al.
8,147,530 B2 4/2012 Strnad et al.
8,167,918 B2 5/2012 Strnad et al.
8,172,848 B2 5/2012 Tomko et al.
8,192,441 B2 6/2012 Collazo
8,197,487 B2 6/2012 Poncet et al.
8,231,623 B1 7/2012 Jordan
8,231,663 B2 7/2012 Kay et al.
8,236,000 B2 8/2012 Ammann et al.
8,246,561 B1 8/2012 Agee et al.
D666,721 S 9/2012 Wright et al.
8,262,664 B2 9/2012 Justin et al.
8,277,459 B2 10/2012 Sand et al.
8,282,644 B2 10/2012 Edwards
8,282,645 B2 10/2012 Lawrence et al.
8,292,966 B2 10/2012 Morton
8,303,596 B2 11/2012 Plassky et al.
8,313,492 B2 11/2012 Wong et al.
8,323,289 B2 12/2012 Re
8,337,503 B2 12/2012 Lian
8,343,159 B2 1/2013 Bennett
8,377,105 B2 2/2013 Buescher
D679,395 S 4/2013 Wright et al.
8,409,209 B2 4/2013 Ammann et al.

(56) References Cited

U.S. PATENT DOCUMENTS

| | | | | |
|---|---|---|---|---|
| 8,435,246 | B2 | 5/2013 | Fisher et al. | |
| 8,475,462 | B2 | 7/2013 | Thomas et al. | |
| 8,496,662 | B2 | 7/2013 | Novak et al. | |
| 8,518,045 | B2 | 8/2013 | Szanto | |
| 8,523,870 | B2 | 9/2013 | Green et al. | |
| 8,529,571 | B2 | 9/2013 | Horan et al. | |
| 8,540,777 | B2 | 9/2013 | Ammann et al. | |
| 8,545,508 | B2 | 10/2013 | Collazo | |
| D694,884 | S | 12/2013 | Mooradian et al. | |
| D695,402 | S | 12/2013 | Dacosta et al. | |
| 8,652,142 | B2 | 2/2014 | Geissler | |
| 8,657,820 | B2 | 2/2014 | Kubiak et al. | |
| D701,303 | S | 3/2014 | Cook | |
| 8,672,945 | B2 | 3/2014 | Lavallee et al. | |
| 8,696,716 | B2 | 4/2014 | Kartalian et al. | |
| 8,702,715 | B2 | 4/2014 | Ammann et al. | |
| D705,929 | S | 5/2014 | Frey | |
| 8,715,363 | B2 | 5/2014 | Ratron et al. | |
| 8,728,084 | B2 | 5/2014 | Berelsman et al. | |
| 8,758,354 | B2 | 6/2014 | Habegger et al. | |
| 8,764,760 | B2 | 7/2014 | Metzger et al. | |
| 8,764,763 | B2 | 7/2014 | Wong et al. | |
| 8,771,279 | B2 | 7/2014 | Philippon et al. | |
| 8,777,948 | B2 | 7/2014 | Bernsteiner | |
| 8,784,427 | B2 | 7/2014 | Fallin et al. | |
| 8,784,457 | B2 | 7/2014 | Graham | |
| 8,795,286 | B2 | 8/2014 | Sand et al. | |
| 8,801,727 | B2 | 8/2014 | Chan et al. | |
| 8,808,303 | B2 | 8/2014 | Stemniski et al. | |
| 8,828,012 | B2 | 9/2014 | May et al. | |
| 8,858,602 | B2 | 10/2014 | Weiner et al. | |
| 8,882,778 | B2 | 11/2014 | Ranft | |
| 8,882,816 | B2 | 11/2014 | Kartalian et al. | |
| 8,888,785 | B2 | 11/2014 | Ammann et al. | |
| D720,456 | S | 12/2014 | Dacosta et al. | |
| 8,900,247 | B2 | 12/2014 | Tseng et al. | |
| 8,906,026 | B2 | 12/2014 | Ammann et al. | |
| 8,945,132 | B2 | 2/2015 | Plassy et al. | |
| 8,998,903 | B2 | 4/2015 | Price et al. | |
| 8,998,904 | B2 | 4/2015 | Zeetser et al. | |
| 9,011,507 | B2 | 4/2015 | Schelling | |
| 9,023,052 | B2 | 5/2015 | Lietz et al. | |
| 9,044,250 | B2 | 6/2015 | Olsen et al. | |
| 9,060,822 | B2 | 6/2015 | Lewis et al. | |
| 9,089,376 | B2 | 7/2015 | Medoff et al. | |
| 9,101,421 | B2 | 8/2015 | Blacklidge | |
| 9,107,715 | B2 | 8/2015 | Blitz et al. | |
| 9,113,920 | B2 | 8/2015 | Ammann et al. | |
| D740,424 | S | 10/2015 | Dacosta et al. | |
| D765,844 | S | 9/2016 | DaCosta | |
| D766,434 | S | 9/2016 | DaCosta | |
| D766,437 | S | 9/2016 | DaCosta | |
| D766,438 | S | 9/2016 | DaCosta | |
| D766,439 | S | 9/2016 | DaCosta | |
| 9,452,057 | B2 | 9/2016 | Dacosta et al. | |
| 9,522,023 | B2 | 12/2016 | Haddad et al. | |
| 9,592,084 | B2 | 3/2017 | Grant | |
| 9,750,538 | B2 | 9/2017 | Soffiatti et al. | |
| 9,785,747 | B2 | 10/2017 | Geebelen | |
| 9,936,994 | B2 * | 4/2018 | Smith .................. | A61B 17/152 |
| 9,980,760 | B2 | 5/2018 | Dacosta et al. | |
| 10,028,750 | B2 | 7/2018 | Rose | |
| 10,064,631 | B2 | 9/2018 | Dacosta et al. | |
| 10,159,499 | B2 | 12/2018 | Dacosta et al. | |
| 10,292,713 | B2 | 5/2019 | Fallin et al. | |
| 10,327,829 | B2 | 6/2019 | Dacosta et al. | |
| 10,376,268 | B2 | 8/2019 | Fallin et al. | |
| 10,470,779 | B2 | 11/2019 | Fallin et al. | |
| 10,779,867 | B2 | 9/2020 | Penzimer et al. | |
| 10,856,886 | B2 | 12/2020 | Dacosta et al. | |
| 10,856,918 | B2 | 12/2020 | Dacosta | |
| 10,939,939 | B1 | 3/2021 | Gil et al. | |
| 11,304,705 | B2 | 4/2022 | Fallin et al. | |
| 2002/0099381 | A1 | 7/2002 | Maroney | |
| 2002/0107519 | A1 | 8/2002 | Dixon et al. | |
| 2002/0165552 | A1 | 11/2002 | Duffner | |
| 2002/0198531 | A1 | 12/2002 | Millard et al. | |
| 2004/0010259 | A1 | 1/2004 | Keller et al. | |
| 2004/0039394 | A1 | 2/2004 | Conti et al. | |
| 2004/0097946 | A1 | 5/2004 | Dietzel et al. | |
| 2004/0138669 | A1 | 7/2004 | Horn | |
| 2005/0004676 | A1 | 1/2005 | Schon et al. | |
| 2005/0033338 | A1 | 2/2005 | Ferree | |
| 2005/0059978 | A1 | 3/2005 | Sherry et al. | |
| 2005/0070909 | A1 | 3/2005 | Egger et al. | |
| 2005/0075641 | A1 | 4/2005 | Singhatat et al. | |
| 2005/0101961 | A1 | 5/2005 | Huebner et al. | |
| 2005/0149042 | A1 | 7/2005 | Metzger | |
| 2005/0228389 | A1 | 10/2005 | Stiernborg | |
| 2005/0251147 | A1 | 11/2005 | Novak | |
| 2005/0267482 | A1 | 12/2005 | Hyde, Jr. | |
| 2005/0273112 | A1 | 12/2005 | McNamara | |
| 2006/0129163 | A1 | 6/2006 | McGuire | |
| 2006/0206044 | A1 | 9/2006 | Simon | |
| 2006/0217733 | A1 | 9/2006 | Plassky et al. | |
| 2006/0229621 | A1 | 10/2006 | Cadmus | |
| 2006/0241607 | A1 | 10/2006 | Myerson et al. | |
| 2006/0241608 | A1 | 10/2006 | Myerson et al. | |
| 2006/0264961 | A1 | 11/2006 | Murray-Brown | |
| 2007/0010818 | A1 | 1/2007 | Stone et al. | |
| 2007/0123857 | A1 | 5/2007 | Deffenbaugh et al. | |
| 2007/0233138 | A1 | 10/2007 | Figueroa et al. | |
| 2007/0265634 | A1 | 11/2007 | Weinstein | |
| 2007/0276383 | A1 | 11/2007 | Rayhack | |
| 2008/0009863 | A1 | 1/2008 | Bond et al. | |
| 2008/0015603 | A1 | 1/2008 | Collazo | |
| 2008/0039850 | A1 | 2/2008 | Rowley et al. | |
| 2008/0091197 | A1 | 4/2008 | Coughlin | |
| 2008/0140081 | A1 | 6/2008 | Heavener et al. | |
| 2008/0147073 | A1 | 6/2008 | Ammann et al. | |
| 2008/0172054 | A1 | 7/2008 | Claypool et al. | |
| 2008/0195215 | A1 | 8/2008 | Morton | |
| 2008/0208252 | A1 | 8/2008 | Holmes | |
| 2008/0243158 | A1 | 10/2008 | Morgan | |
| 2008/0262500 | A1 | 10/2008 | Collazo | |
| 2008/0269908 | A1 | 10/2008 | Warburton | |
| 2008/0288004 | A1 | 11/2008 | Schendel | |
| 2009/0036893 | A1 | 2/2009 | Kartalian et al. | |
| 2009/0036931 | A1 | 2/2009 | Pech et al. | |
| 2009/0054899 | A1 | 2/2009 | Ammann et al. | |
| 2009/0093849 | A1 | 4/2009 | Grabowski | |
| 2009/0105767 | A1 | 4/2009 | Reiley | |
| 2009/0112212 | A1 | 4/2009 | Murray et al. | |
| 2009/0118733 | A1 | 5/2009 | Orsak et al. | |
| 2009/0198244 | A1 | 8/2009 | Leibel | |
| 2009/0198279 | A1 | 8/2009 | Zhang et al. | |
| 2009/0216089 | A1 | 8/2009 | Davidson | |
| 2009/0222047 | A1 | 9/2009 | Graham | |
| 2009/0254092 | A1 | 10/2009 | Albiol Llorach | |
| 2009/0254126 | A1 | 10/2009 | Orbay et al. | |
| 2009/0287309 | A1 | 11/2009 | Walch et al. | |
| 2010/0069910 | A1 | 3/2010 | Hasselman | |
| 2010/0121334 | A1 | 5/2010 | Couture et al. | |
| 2010/0125300 | A1 * | 5/2010 | Blitz .................. | A61B 17/8085<br>606/283 |
| 2010/0130981 | A1 | 5/2010 | Richards | |
| 2010/0152782 | A1 | 6/2010 | Stone et al. | |
| 2010/0168799 | A1 | 7/2010 | Schumer | |
| 2010/0185245 | A1 | 7/2010 | Paul et al. | |
| 2010/0249779 | A1 | 9/2010 | Hotchkiss et al. | |
| 2010/0256687 | A1 | 10/2010 | Neufeld et al. | |
| 2010/0318088 | A1 | 12/2010 | Warne et al. | |
| 2010/0324556 | A1 | 12/2010 | Tyber et al. | |
| 2011/0009865 | A1 | 1/2011 | Orfaly | |
| 2011/0093084 | A1 | 4/2011 | Morton | |
| 2011/0118739 | A1 | 5/2011 | Tyber et al. | |
| 2011/0178524 | A1 | 7/2011 | Lawrence et al. | |
| 2011/0245835 | A1 | 10/2011 | Dodds et al. | |
| 2011/0288550 | A1 | 11/2011 | Orbay et al. | |
| 2011/0301648 | A1 | 12/2011 | Lofthouse et al. | |
| 2012/0016426 | A1 | 1/2012 | Robinson | |
| 2012/0065689 | A1 | 3/2012 | Prasad et al. | |
| 2012/0078258 | A1 | 3/2012 | Lo et al. | |
| 2012/0123420 | A1 | 5/2012 | Honiball | |

(56) References Cited

U.S. PATENT DOCUMENTS

| | | | |
|---|---|---|---|
| 2012/0123484 | A1 | 5/2012 | Lietz et al. |
| 2012/0130376 | A1 | 5/2012 | Loring et al. |
| 2012/0130382 | A1 | 5/2012 | Iannotti et al. |
| 2012/0130383 | A1 | 5/2012 | Budoff |
| 2012/0184961 | A1 | 7/2012 | Johannaber |
| 2012/0185056 | A1 | 7/2012 | Warburton |
| 2012/0191199 | A1 | 7/2012 | Raemisch |
| 2012/0239045 | A1 | 9/2012 | Li |
| 2012/0253350 | A1 | 10/2012 | Anthony et al. |
| 2012/0265301 | A1 | 10/2012 | Demers et al. |
| 2012/0277745 | A1 | 11/2012 | Lizee |
| 2012/0303033 | A1 | 11/2012 | Weiner et al. |
| 2012/0330135 | A1 | 12/2012 | Millahn et al. |
| 2013/0012949 | A1 | 1/2013 | Fallin et al. |
| 2013/0035694 | A1 | 2/2013 | Grimm et al. |
| 2013/0085499 | A1 | 4/2013 | Lian |
| 2013/0085502 | A1 | 4/2013 | Harrold |
| 2013/0096563 | A1 | 4/2013 | Meade et al. |
| 2013/0131821 | A1 | 5/2013 | Cachia |
| 2013/0150900 | A1 | 6/2013 | Haddad et al. |
| 2013/0150903 | A1 | 6/2013 | Vincent |
| 2013/0158556 | A1 | 6/2013 | Jones et al. |
| 2013/0165936 | A1 | 6/2013 | Myers |
| 2013/0165938 | A1 | 6/2013 | Chow et al. |
| 2013/0172942 | A1 | 7/2013 | Lewis et al. |
| 2013/0184714 | A1 | 7/2013 | Kaneyama et al. |
| 2013/0190765 | A1 | 7/2013 | Harris et al. |
| 2013/0190766 | A1 | 7/2013 | Harris et al. |
| 2013/0204259 | A1 | 8/2013 | Zajac |
| 2013/0226248 | A1 | 8/2013 | Hatch et al. |
| 2013/0226252 | A1 | 8/2013 | Mayer |
| 2013/0231668 | A1 | 9/2013 | Olsen et al. |
| 2013/0237987 | A1 | 9/2013 | Graham |
| 2013/0237989 | A1 | 9/2013 | Bonutti |
| 2013/0267956 | A1 | 10/2013 | Terrill et al. |
| 2013/0310836 | A1 | 11/2013 | Raub et al. |
| 2013/0325019 | A1 | 12/2013 | Thomas et al. |
| 2013/0325076 | A1 | 12/2013 | Palmer et al. |
| 2013/0331845 | A1 | 12/2013 | Horan et al. |
| 2013/0338785 | A1 | 12/2013 | Wong |
| 2014/0005672 | A1 | 1/2014 | Edwards et al. |
| 2014/0025127 | A1 | 1/2014 | Richter |
| 2014/0039501 | A1 | 2/2014 | Schickendantz et al. |
| 2014/0039561 | A1 | 2/2014 | Weiner et al. |
| 2014/0046387 | A1 | 2/2014 | Waizenegger |
| 2014/0074099 | A1 | 3/2014 | Vigneron et al. |
| 2014/0074101 | A1 | 3/2014 | Collazo |
| 2014/0094861 | A1 | 4/2014 | Fallin |
| 2014/0094924 | A1 | 4/2014 | Hacking et al. |
| 2014/0135775 | A1 | 5/2014 | Maxson et al. |
| 2014/0163563 | A1 | 6/2014 | Reynolds et al. |
| 2014/0171953 | A1 | 6/2014 | Gonzalvez et al. |
| 2014/0180342 | A1 | 6/2014 | Lowery et al. |
| 2014/0188139 | A1 | 7/2014 | Fallin et al. |
| 2014/0194884 | A1 | 7/2014 | Martin et al. |
| 2014/0194999 | A1 | 7/2014 | Orbay et al. |
| 2014/0207144 | A1 | 7/2014 | Lee et al. |
| 2014/0249537 | A1 | 9/2014 | Wong et al. |
| 2014/0257308 | A1 | 9/2014 | Johannaber |
| 2014/0257509 | A1 | 9/2014 | Dacosta et al. |
| 2014/0276815 | A1 | 9/2014 | Riccione |
| 2014/0276853 | A1 | 9/2014 | Long et al. |
| 2014/0277176 | A1 | 9/2014 | Buchanan et al. |
| 2014/0277214 | A1 | 9/2014 | Helenbolt et al. |
| 2014/0288562 | A1 | 9/2014 | Von Zabern et al. |
| 2014/0296995 | A1 | 10/2014 | Reiley et al. |
| 2014/0303621 | A1 | 10/2014 | Gerold et al. |
| 2014/0336658 | A1 | 11/2014 | Luna et al. |
| 2014/0343555 | A1 | 11/2014 | Russi et al. |
| 2014/0350561 | A1 | 11/2014 | Dacosta et al. |
| 2015/0032168 | A1 | 1/2015 | Orsak et al. |
| 2015/0045801 | A1 | 2/2015 | Axelson, Jr. et al. |
| 2015/0045839 | A1 | 2/2015 | Dacosta et al. |
| 2015/0051650 | A1 | 2/2015 | Verstreken et al. |
| 2015/0057667 | A1 | 2/2015 | Ammann et al. |
| 2015/0066094 | A1 | 3/2015 | Prandi et al. |
| 2015/0112446 | A1 | 4/2015 | Melamed et al. |
| 2015/0119944 | A1 | 4/2015 | Geldwert |
| 2015/0142064 | A1 | 5/2015 | Perez et al. |
| 2015/0150608 | A1 | 6/2015 | Sammarco |
| 2015/0182273 | A1 | 7/2015 | Stemniski et al. |
| 2015/0223851 | A1 | 8/2015 | Hill et al. |
| 2015/0245858 | A1 | 9/2015 | Weiner et al. |
| 2016/0015426 | A1 | 1/2016 | Dayton |
| 2016/0022315 | A1 | 1/2016 | Soffiatti et al. |
| 2016/0135858 | A1 | 5/2016 | Dacosta et al. |
| 2016/0151165 | A1 | 6/2016 | Fallin et al. |
| 2016/0175089 | A1 | 6/2016 | Fallin et al. |
| 2016/0192950 | A1 | 7/2016 | Dayton et al. |
| 2016/0192970 | A1 | 7/2016 | Dayton et al. |
| 2016/0199076 | A1 | 7/2016 | Fallin et al. |
| 2016/0213384 | A1 | 7/2016 | Fallin et al. |
| 2016/0235414 | A1 | 8/2016 | Hatch et al. |
| 2016/0242791 | A1 | 8/2016 | Fallin et al. |
| 2016/0256204 | A1 | 9/2016 | Patel et al. |
| 2016/0324532 | A1 | 11/2016 | Montoya et al. |
| 2016/0338697 | A1 | 11/2016 | Biedermann et al. |
| 2016/0354127 | A1 | 12/2016 | Lundquist et al. |
| 2017/0014143 | A1 | 1/2017 | Dayton et al. |
| 2017/0014173 | A1 | 1/2017 | Smith et al. |
| 2017/0042598 | A1 | 2/2017 | Santrock et al. |
| 2017/0042599 | A1 * | 2/2017 | Bays .................. A61B 17/8061 |
| 2017/0079669 | A1 | 3/2017 | Bays et al. |
| 2017/0143511 | A1 | 5/2017 | Cachia |
| 2017/0164989 | A1 | 6/2017 | Weiner et al. |
| 2018/0000508 | A1 | 1/2018 | Hu et al. |
| 2018/0132868 | A1 | 5/2018 | Dacosta et al. |
| 2018/0289379 | A1 | 10/2018 | Dacosta et al. |
| 2018/0344334 | A1 | 12/2018 | Kim et al. |
| 2020/0015874 | A1 | 1/2020 | Hartson et al. |
| 2020/0229828 | A1 | 7/2020 | Wagner et al. |
| 2020/0237387 | A1 | 7/2020 | Luttrell et al. |
| 2020/0330109 | A1 | 10/2020 | Woodard et al. |
| 2020/0390463 | A1 | 12/2020 | Burroughs, III |
| 2021/0030513 | A1 | 2/2021 | Pajunk-Schelling et al. |
| 2024/0122752 | A1 | 4/2024 | Micheletti |

FOREIGN PATENT DOCUMENTS

| | | | |
|---|---|---|---|
| CA | 2854997 | A1 | 5/2013 |
| CH | 695846 | A5 | 9/2006 |
| CN | 2930668 | Y | 8/2007 |
| CN | 201558162 | U | 8/2010 |
| CN | 201572172 | U | 9/2010 |
| CN | 201586060 | U | 9/2010 |
| CN | 201912210 | U | 8/2011 |
| CN | 101237835 | B | 11/2012 |
| CN | 202801773 | U | 3/2013 |
| CN | 103462675 | A | 12/2013 |
| CN | 103505276 | A | 1/2014 |
| CN | 203458450 | U | 3/2014 |
| CN | 103735306 | A | 4/2014 |
| CN | 102860860 | B | 5/2014 |
| CN | 203576647 | U | 5/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |

(56) References Cited

FOREIGN PATENT DOCUMENTS

| | | | |
|---|---|---|---|
| EP | 2750617 | A1 | 7/2014 |
| EP | 2849684 | A1 | 3/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 2154143 | A | 9/1985 |
| GB | 2154144 | A | 9/1985 |
| GB | 2334214 | B | 1/2003 |
| IN | 200903719 | P1 | 6/2009 |
| IN | 200904479 | P2 | 5/2010 |
| IN | 140/DELNP/2012 | P1 | 2/2013 |
| IN | 2004/KOLNP/2013 | P2 | 11/2013 |
| JP | S635739 | A | 1/1988 |
| JP | H0531116 | A | 2/1993 |
| JP | 2004174265 | A | 6/2004 |
| JP | 2006158972 | A | 6/2006 |
| JP | 4134243 | B2 | 8/2008 |
| JP | 2008537498 | A | 9/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| MD | 756 | Z | 11/2014 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012029008 | A1 | 3/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015127515 | A2 | 9/2015 |
| WO | 2016134160 | A1 | 8/2016 |
| WO | 2020180598 | A1 | 9/2020 |

OTHER PUBLICATIONS

Penn State Industries PKSRB124 Small Deluxe Replacement Seam Ripper Blade, amazon.com, first available Feb. 3, 2020 [online], [ site visited Mar. 19, 2024], Available from internet, URL: https://www.amazon.com/Penn-State-Industries-PKSRB124-Replacement/dp/B084GDG3V6 (Year: 2020).

Lapiplasty, SpeedRelease and TriTome Sales Sheet, lapiplasty.com, first available 2022 [online], [site visited Mar. 19, 2024], Available from internet, URL: https://www.lapiplasty.com/uploads/2022/08/M1969B_Speed Release-and-TriTome _Sales-Sheet. pdf (Year: 2022).

Brother XF4967001 Seam Ripper, allbrands.com, [online], [site visited Mar. 19, 2024], Available from internet, URL: https://www.allbrands.com/products/14360-brother-xf4967001-seam-ripper-for-sewing-serging-q (Year: 2024).

Janome Seam Ripper, Janome.com, [online], [site visited Mar. 19, 2024], Available from internet, URL: https://www.janome.com/accessories/accessories/seam-ripper/ (Year: 2024).

"Accu-Cut Osteotomy Guide System," BioPro, Brochure, Oct. 2018, 2 pages.

"Acumed Osteotomiesystem Operationstechnik," Acumed, 2014, 19 pages (including 3 pages English translation).

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

Alvine et al., "Peg and Dowel Fusion of the Proximal Interphalangeal Joint," Foot & Ankle, vol. 1, No. 2, 1980, pp. 90-94.

Anderson et al., "Uncemented STAR Total Ankle Prostheses," The Journal of Bone and Joint Surgery, vol. 86(1, Suppl 2), Sep. 2004, pp. 103-111, (Abstract Only).

Bednarz et al., "Modified Lapidus Procedure for the Treatment of Hypermobile Hallux Valgus," Foot & Ankle International, vol. 21, No. 10, Oct. 2000, pp. 816-821.

Blomer, "Knieendoprothetik—Herstellerische Probleme und technologische Entwicklungen," Orthopade, vol. 29, 2000, pp. 688-696, including English Abstract on p. 689.

Bouaicha et al., "Fixation of Maximal Shift Scarf Osteotomy with Inside-Out Plating: Technique Tip," Foot & Ankle International, vol. 32, No. 5, May 2011, pp. 567-569.

Carr et al., "Correctional Osteotomy for Metatarsus Primus Varus and Hallux Valgus," The Journal of Bone and Joint Surgery, vol. 50-A, No. 7, Oct. 1968, pp. 1353-1367.

Coetzee et al., "The Lapidus Procedure: A Prospective Cohort Outcome Study," Foot & Ankle International, vol. 25, No. 8, Aug. 2004, pp. 526-531.

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

Doty et al., "Hallux valgus and hypermobility of the first ray: facts and fiction," International Orthopaedics, vol. 37, 2013, pp. 1655-1660.

(56) References Cited

OTHER PUBLICATIONS

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
"Futura Forefoot Implant Arthroplasty Products," Tornier, Inc., 2008, 14 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Garthwait, "Accu-Cut System Facilitates Enhanced Precision," Podiatry Today, vol. 18, No. 6, Jun. 2005, 6 pages.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).
"Hat-Trick Lesser Toe Repair System," Smith & Nephew, Brochure, Aug. 2014, 12 pages.
"Hat-Trick Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
"Hoffmann II Compact External Fixation System," Stryker, Brochure, Literature No. 5075-1-500, 2006, 12 pages.
"Hoffmann II Micro Lengthener," Stryker, Operative Technique, Literature No. 5075-2-002, 2008, 12 pages.
"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
"Lag Screw Target Bow," Stryker Leibinger GmbH & Co. KG, Germany 2004, 8 pages.
Lapidus, "The Author's Bunion Operation From 1931 to 1959," Clinical Orthopaedics, vol. 16, 1960, pp. 119-135.
Lieske et al., "Implantation einer Sprunggelenktotalendo-prothese vom Typ Salto 2," Operative Orthopädie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Computernavigierter Gelenkersatz am Knie mit dem Orthopilot," Operative Orthopädie und Traumatologie, vol. 22, No. 1, 2010, pp. 63-80, including English Abstract on p. 64.
Magin, "Die belastungsstabile Lapidus-Arthrodese bei Hallux-valgus-Deformität mittels IVP-Plattenfixateur (V-TEK-System)," Operative Orthopädie und Traumatologie, vol. 26, No. 2, 2014, pp. 184-195, including English Abstract on p. 186.
Michelangelo Bunion System, Surgical Technique, Instratek Incorporated, publication date unknown, 4 pages.
Mini Joint Distractor, Arthrex, retrieved Dec. 19, 2014, from the Internet: <http://www.arthrex.com/foot-ankle/mini-joint-distractor/products>, 2 pages.
MiniRail System, Small Bone Innovations, Surgical Technique, 2010, 24 pages.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Modular Rail System: External Fixator, Smith & Nephew, Surgical Technique, 2013, 44 pages.
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and the BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Otsuki et al., "Developing a novel custom cutting guide for curved per-acetabular osteotomy," International Orthopaedics (SICOT), vol. 37, 2013, pp. 1033-1038.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Rx-Fix Mini Rail External Fixator, Wright Medical Technology, Brochure, Aug. 15, 2014, 2 pages.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.

(56) References Cited

OTHER PUBLICATIONS

Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
"Smith & Nephew scores a Hat-Trick with its entry into the high-growth hammer toe repair market," Smith & Nephew, Jul. 31, 2014, 2 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weber et al., "A Simple System for Navigation of Bone Alignment Osteotomies of the Tibia," International Congress Series, vol. 1268, Jan. 2004, pp. 608-613, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Boffeli et al., "Can We Abandon Saw Wedge Resection in Lapidus Fusion? A Comparative Study of Joint Preparation Techniques Regarding Correction of Deformity, Union Rate, and Preservation of First Ray Length," The Journal of Foot and Ankle Surgery, vol. 58, No. 6, Nov. 2019, published online: Sep. 25, 2019, pp. 1118-1124.
Conti et al., "Effect of the Modified Lapidus Procedure on Pronation of the First Ray in Hallux Valgus," Foot & Ankle International, Feb. 1, 2020, published online: Oct. 16, 2019, 8 pages.
Conti et al., "Effect of the Modified Lapidus Procedure for Hallux Valgus on Foot Width," Foot & Ankle International, Feb. 1, 2020, published online: Oct. 30, 2019, 6 pages.
Cruz et al., "Does Hallux Valgus Exhibit a Deformity Inherent to the First Metatarsal Bone?" The Journal of Foot & Ankle Surgery, vol. 58, No. 6, Nov. 2019, pp. 1210-1214.
Dahlgren et al., "First Tarsometatarsal Fusion Using Saw Preparation vs. Standard Preparation of the Joint: A Cadaver Study," Foot & Ankle Orthopaedics, vol. 4, No. 4, Oct. 2019, 2 pages.
Hatch et al., "Triplane Hallux Abducto Valgus Classification," The Journal of Foot & Ankle Surgery, vol. 57, No. 5, Sep./Oct. 2018, published online: May 18, 2018, pp. 972-981.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Li et al., "Evolution of Thinking of the Lapidus Procedure and Fixation," Foot and Ankle Clinics, vol. 25, No. 1, Mar. 2020, published online: Dec. 16, 2019, pp. 18 pages.
Lopez et al., "Metatarsalgia: Assessment Algorithm and Decision Making," Foot and Ankle Clinics, vol. 24, No. 4, Dec. 2019, published online: Sep. 25, 2019, pp. 561-569.
Ray et al., "Multicenter Early Radiographic Outcomes of Triplanar Tarsometatarsal Arthrodesis With Early Weightbearing," Foot & Ankle International, vol. 40, No. 8, Aug. 1, 2019, published online: May 5, 2019, 7 pages.
Walker et al., "The Role of First Ray Insufficiency in the Development of Metatarsalgia," Foot and Ankle Clinics, vol. 24, No. 4, Dec. 2019, published online: Sep. 5, 2019, pp. 641-648.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Groves, "Operative Report," St. Tammany Parish Hospital, Date of Procedure, Mar. 26, 2014, 2 pages.
D'Amico et al., "Motion of the First Ray: Clarification Through Investigation," Journal of the American Podiatry Association, vol. 69, No. 1, Jan. 1979, pp. 17-23.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Mizuno et al., "Detorsion Osteotomy of the First Metatarsal Bone in Hallux Valgus," Japanese Orthopaedic Association, Tokyo, 1956; 30:813-819.
Eustace et al., "Hallux valgus, first metatarsal pronation and collapse of the medial longitudinal arch—a radiological correlation," Skeletal Radiology, vol. 23, 1994, pp. 191-194.

(56) References Cited

OTHER PUBLICATIONS

Collan et al., "The biomechanics of the first metatarsal bone in hallux valgus: A preliminary study utilizing a weight bearing extremity CT," Foot and Ankle Surgery, vol. 19, 2013, pp. 155-161.
Le et al., "Tarsometatarsal Arthrodesis," Operative Techniques in Foot and Ankle Surgery, Section II, Chapter 40, 2011, pp. 281-285.
Coetzee et al., "Revision Hallux Valgus Correction," Operative Techniques in Foot and Ankle Surgery, Section I, Chapter 15, 2011, pp. 84-96.
"Foot and Ankle Instrument Set," Smith & Nephew, 2013, 2 pages.
"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
DiDomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, U.S. Appl. No. 62/118,378, filed Feb. 19, 2015, 62 pages.
Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.
Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, pp. 376-391.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus," The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation for Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.

(56) References Cited

OTHER PUBLICATIONS

Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
"Anatomy of the Foot and Ankle," OrthoPaedia, Retrieved online from <https://orthopaedia.com/page/Anatomy-of-the-Foot-Ankle> on Feb. 21, 2022, 21 pages.
Farac et al., "Arthroscopy of the Great and Lesser Toes," Musculoskeletal Key, Retrieved online from <https://musculoskeletalkey.com/arthroscopy-of-the-great-and-lesser-toes/> on Feb. 18, 2022, dated Sep. 25, 2018, 7 pages.
Awh, "Turf Toe," Radsource, MRI Web Clinic, Retrieved online from <https://radsource.us/clinic-turf-toe/>, dated Jan. 2012, 20 pages.
"Integra Jarit Surgical Instruments," Integra, 2011, 916 pages.

* cited by examiner

FIRST METATARSAL LATERAL RELEASE INSTRUMENT AND TECHNIQUE

CROSS-REFERENCE

This application claims the benefit of U.S. Provisional Patent Application No. 63/313,131, filed Feb. 23, 2022, the entire contents of which are incorporated herein by reference.

TECHNICAL FIELD

This disclosure relates to instruments and techniques for performing a bone realignment procedure and, more particularly, to instruments and techniques for releasing a bone to allow the bone to be repositioned.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

In some cases, surgical intervention is needed to address hallux valgus and/or other bone deformities. Surgical intervention may involve realigning one or more bones of the foot, improving patient comfort and increasing patient mobility. A clinician may use a variety of different surgical instruments during a surgical procedure performed on the foot, including one or more cutting instruments to cut tissue and/or bone. Surgical instruments that can facilitate efficient, accurate, and reproducible clinical results are useful for practitioners performing bone realignment techniques.

SUMMARY

In general, this disclosure is directed to orthopedic cutting instruments and associated systems and techniques utilizing such cutting instruments. In some examples, an orthopedic cutting instrument according to the disclosure can be used to cut and release soft tissue, such as ligaments, on the lateral side of the first metatarsal bone of the foot. This can help mobilize the first metatarsal for subsequent realignment, e.g., by cutting soft tissue connected to the first metatarsal that otherwise inhibits repositioning of the bone during a realignment procedure.

For example, during a metatarsal realignment procedure, a clinician may surgically access the joint capsule of the metatarsophalangeal joint between the distal end of the first metatarsal and proximal end of the proximal phalanx. The clinician may use a scalpel to cut into the lateral side of the joint capsule exposing soft tissue, such as one or more sesamoidal ligaments, on the lateral side of the first metatarsal. The clinician can then utilize a cutting instrument according to the disclosure to cut soft tissue accessed through the incision made in the joint capsule. The clinician can insert the head of the cutting instrument through the incision in the skin and joint capsule and use the head of the cutting instrument to selectively capture and cut targeted soft tissue.

In some implementations, a cutting instrument according to disclosure is configured with a cutting surface and a guiding projection extending outwardly relative to the cutting surface. The guiding projection may be a region of comparatively smaller cross-sectional area than the overall cutting head of the cutting instrument. For example, the guiding projection may be defined by a cylinder, a rectangle, and/or projection having other cross-sectional shape extending outwardly from a remainder of the cutting head. The guiding projection may terminate in a blunt distal end not configured to cut tissue. A cutting surface can be provided that is set back from the distal end of the guiding projection.

In use, the clinician can advance the guiding projection of the cutting head into an incision through the skin of the patient toward target soft tissue to be cut, such as one or more ligaments to be cut. The clinician can advance the guiding projection under the soft tissue to be cut, e.g., placing the guiding projection between the soft tissue to be cut and underlying soft tissue and/or bone not intended to be cut. In the process, the clinician can capture the soft tissue to be cut between the guiding projection and the cutting surface of the cutting instrument. The clinician may then further advance the cutting instrument, causing the captured soft tissue to be cut by the cutting surface. In this way, the cutting instrument can allow the clinician to accurately target soft tissue to be cut using the cutting instrument, helping to avoid inadvertent or untargeted cutting that may otherwise occur if merely plunging a scalpel into the general region of the tissue intended to be cut.

In one example, a method of releasing a first metatarsal for realignment is described. The method includes surgically accessing a sesamoidal ligament in a foot of a patient and advancing a guiding projection of a cutting instrument under the sesamoidal ligament, thereby capturing the sesamoidal ligament between the guiding projection of the cutting instrument and a cutting surface of the cutting instrument recessed relative to a distal end of the guide projection. The method also involves subsequently cutting the sesamoidal ligament with the cutting surface of the cutting instrument.

In another example, a method of realigning at least a portion of a first metatarsal is described. The method includes surgically accessing a sesamoidal ligament in a foot of a patient and advancing a guiding projection of a cutting instrument under the sesamoidal ligament, thereby capturing the sesamoidal ligament between the guiding projection of the cutting instrument and a cutting surface of the cutting instrument recessed relative to a distal end of the guide projection. The method includes subsequently cutting the sesamoidal ligament with the cutting surface of the cutting instrument. The method also involves moving at least a portion of a first metatarsal in at least one plane and fixating a moved position of the portion of the first metatarsal by applying at least one bone fixation device.

In another example, an instrument configured for cutting tissue to mobilize a first metatarsal in a foot is described. The instrument includes a handle extending from a first end to a second end and a cutting head on the second end of the handle. The example specifies that the cutting head includes a cutting surface and a guiding projection that terminates in a distal end. According to the example, the cutting surface is recessed relative to the distal end of the guiding projection, and the cutting head is sized to be inserted into an intermetatarsal space between a first metatarsal and a second metatarsal of a foot.

The details of one or more examples are set forth in the accompanying drawings and the description below. Other features, objects, and advantages will be apparent from the description and drawings, and from the claims.

DETAILED DESCRIPTION

Figure 1A:
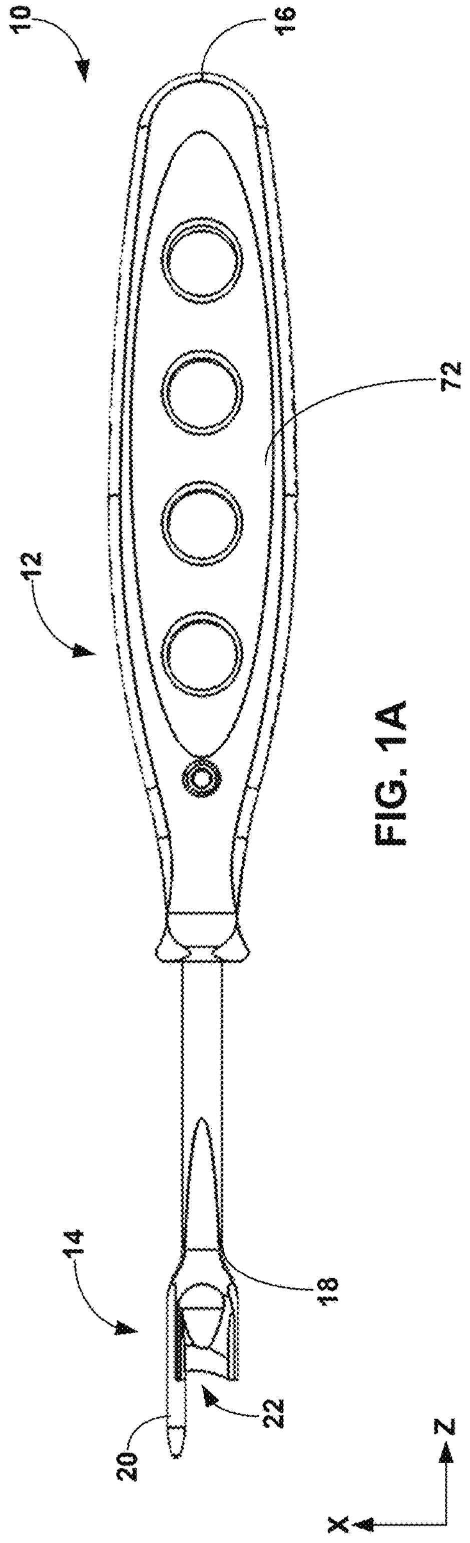
FIG. 1A is a side view an example orthopedic cutting instrument according to the disclosure.

This disclosure generally relates orthopedic cutting instruments and associated systems (e.g., kits) and techniques incorporating one or more such cutting instruments. In some examples, a cutting instrument according to the disclosure can be used cut one or more ligaments and/or other soft tissue for mobilizing a bone for subsequent realignment. For example, the cutting instrument may be used to perform a lateral release during a metatarsal realignment procedure. In these applications, the cutting instrument can be used to cut one or more ligaments and/or other soft tissue on the lateral side of the metatarsal, e.g., adjacent the distal head of the metatarsal. For example, the instrument can be inserted through an incision accessing an intermetatarsal space between a first metatarsal and an adjacent second metatarsal to cut one or more ligaments and/or other targeted tissue in the intermetatarsal space. This can mobilize the first metatarsal for subsequent realignment of the entire metatarsal or portion thereof (e.g. distal portion of the metatarsal when performing an osteotomy that cuts the metatarsal into proximal and distal portions) in one or more planes. While the instrument may find particular utility for performing a lateral release of a first metatarsal, in practice, the clinician can use the instrument to cut any targeted soft tissue, including for releasing other bones and/or joints in the foot, without departing from the scope of the disclosure.

In exemplary applications, the devices, systems, and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing devices and/or techniques of the disclosure can be performed to correct an alignment between a metatarsal (e.g. a first metatarsal) and a cuneiform (e.g., a medial cuneiform), such as a bunion correction. An example of such a procedure is a lapidus procedure. In another example, the devices, systems, and/or techniques can be utilized when modifying a position of one portion of a bone relative to another portion of the same bone. An example of such a procedure is an osteotomy procedure (e.g., metatarsal osteotomy procedure) in which the bone is cut into at least two different bones and one portion (e.g., a distal portion) is realigned relative to another bone portion (e.g., a proximal portion) of the same bone.

Preparation and realignment of one or more bones or bone portions may be performed according to the disclosure for a variety of clinical reasons and indications. Preparation, realignment, and fusion of one bone (or portion thereof) relative to another bone (or portion thereof) may be performed to treat metatarsus hallux valgus and/or other bone and/or joint conditions. Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux adductus angle, the angle between the long axes of the first metatarsal and proximal phalanx in the transverse plane. An increase in the hallux adductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced, e.g., laterally relative to the first metatarsophalangeal joint, resulting in subluxation of the joints between the sesamoid bones and the head of the first metatarsal. This can increase the pressure between the medial sesamoid and the crista of the first metatarsal head.

While techniques and devices are generally described herein in connection with the first metatarsal and medial cuneiform of the foot, the techniques and devices may be used on other adjacent bones (e.g., separated from each other by a joint) and/or adjacent bone portions (e.g., portions of the same bone separated from each other by a fracture or osteotomy). In various examples, the devices, systems, and/or techniques of the disclosure may be utilized on comparatively small bones in the foot such as a metatarsal (e.g., first, second, third, fourth, or fifth metatarsal), a cuneiform (e.g., medial, intermediate, lateral), a cuboid, a phalanx (e.g., proximal, intermediate, distal), and/or combinations thereof. The bones may be separated from each other by a tarsometatarsal ("TMT") joint, a metatarsophalangeal ("MTP") joint, an intermetatarsal space, or other joint or bone space. Accordingly, reference to a first metatarsal and medial cuneiform herein may be replaced with other bone pairs as described herein.

The anatomy of the foot and example techniques utilizing a cutting instrument according to the disclosure will be described in greater detail with respect to FIGS. 3-10. However, an example orthopedic cutting instrument according to the disclosure will first be described with respect to FIGS. 1 and 2.

Figure 1B:
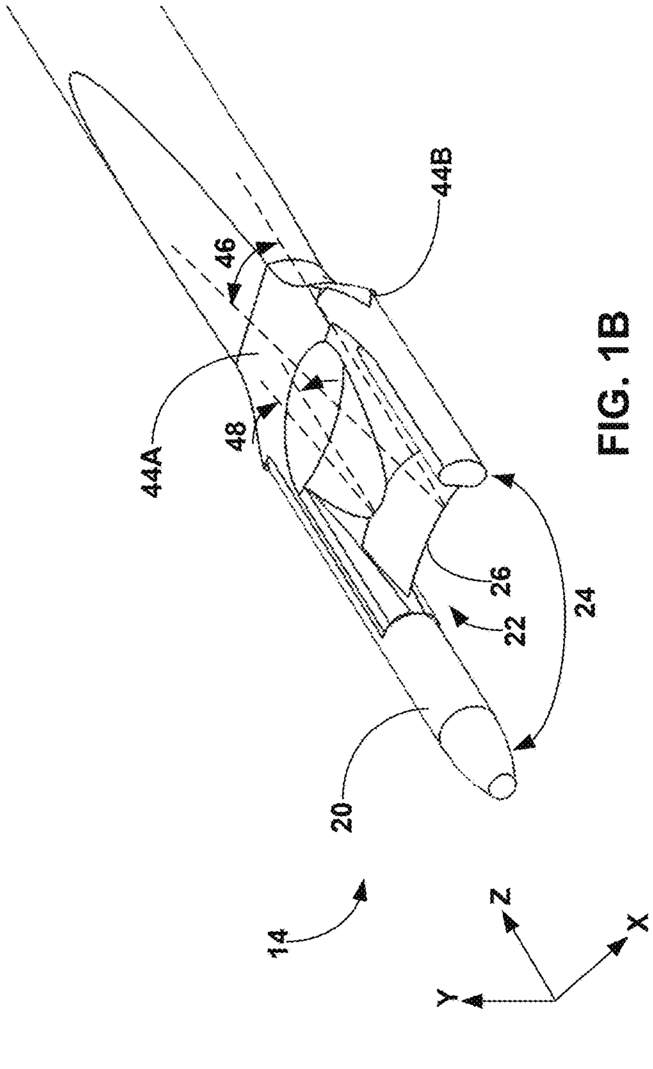
FIG. 1B is an enlarged perspective view of a cutting head of the cutting instrument of FIG. 1B.

FIG. 1A is a side view an example orthopedic cutting instrument 10 according to the disclosure. FIG. 1B is an enlarged perspective view of a cutting head of the cutting instrument. In the illustrated example of FIGS. 1A and 1B, cutting instrument 10 includes a handle 12 and a cutting head 14 operatively connected to the handle. For example, in the illustrated configuration, handle 12 has a major length extending from a first end 16 to a second end 18. Cutting head 14 is connected to and extends from the second end 18 of handle 12. In various implementations, handle 12 and cutting head 14 may be fabricated as a unitary body (e.g., cut or cast as a single piece of material) or may be fabricated as separate components that are joined together to form a combined structure the does not separate during use.

As will be described in greater detail below, cutting head 14 can include a guiding projection 20 and a cutting surface 22. Guiding projection 20 extends outwardly relative to cutting surface 22. As a result, cutting surface 22 is recessed relative to a distal end of guiding projection 20. In use, a clinician can advance a cutting head 14 of cutting instrument 10 toward target tissue to be cut, such as one or more ligaments to be cut. The clinician can use guiding projection 20 to guide forward movement of the cutting instrument. The clinician can advance cutting head 14 toward soft tissue targeted for cutting, such as one or more ligaments, and position guiding projection 20 under the one or more ligaments to be cut. For example, the clinician can advance guiding projection 20 between the one or more ligaments to be cut and underlying soft tissue and/or bone. This can capture the targeted tissue (e.g., one or more ligaments) in a notch 24 formed between guiding projection 20 and cutting surface 22. With the targeted tissue captured in notch 24, the clinician may push cutting instrument 10 further forward, causing cutting surface 22 of the cutting instrument to slice through the tissue captured in the notch. In this way, cutting instrument 10 can allow the clinician to precisely cut targeted tissue, such as one or more ligaments, without inadvertently cutting surrounding tissue not targeted to be cut.

While cutting instrument 10 can be used for any desired surgical procedure, in some configurations, the cutting instrument is configured (e.g., sized and shaped) to facilitate cutting within a joint space between opposed bones of the foot. For example, cutting head 14 of cutting instrument 10 may be configured to be inserted into an intermetatarsal space between a first metatarsal and an adjacent second metatarsal. The clinician may insert cutting head 14 of cutting instrument 10 into the target joint space(s) to cut soft tissue (e.g., muscles, tendons, ligaments, and/or facia) within the joint space. Such soft tissue may be connectively attached to one or more bones (e.g., metatarsal, sesamoid) intended to be realigned. Cutting the soft tissue using cutting instrument 10 can mobilize the bone for subsequent realignment. For example, cutting the soft tissue using cutting instrument 10 can mobilize the bone for subsequent rotation in the frontal plane and/or movement in the transverse plane. After realignment and other associated surgical steps, a realigned bone may be permanently fixated in a moved position using a fixation device to promote fusion of the realigned bone.

Figure 2A:
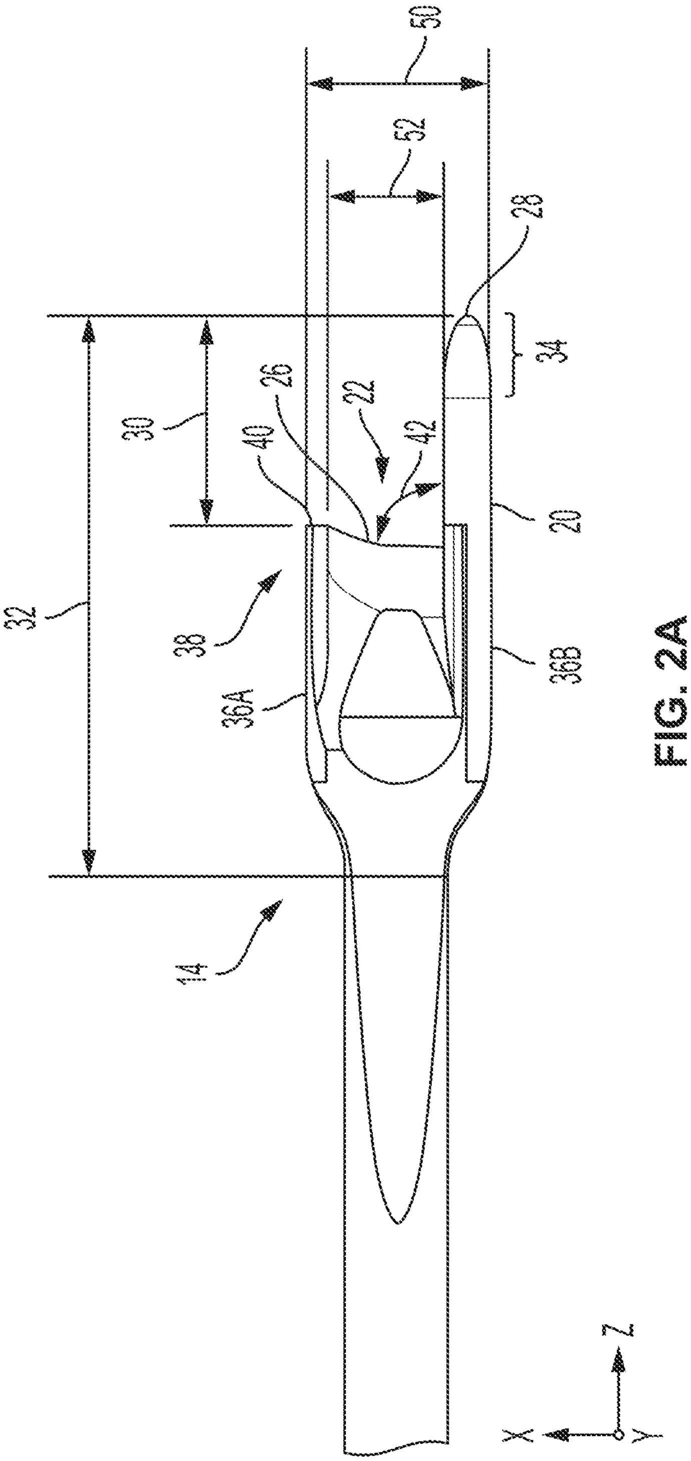
FIGS. 2A and 2B an enlarged side view and bottom view, respectively, of the cutting head of the cutting instrument in FIGS. 1A and 1B.
Figure 2B:
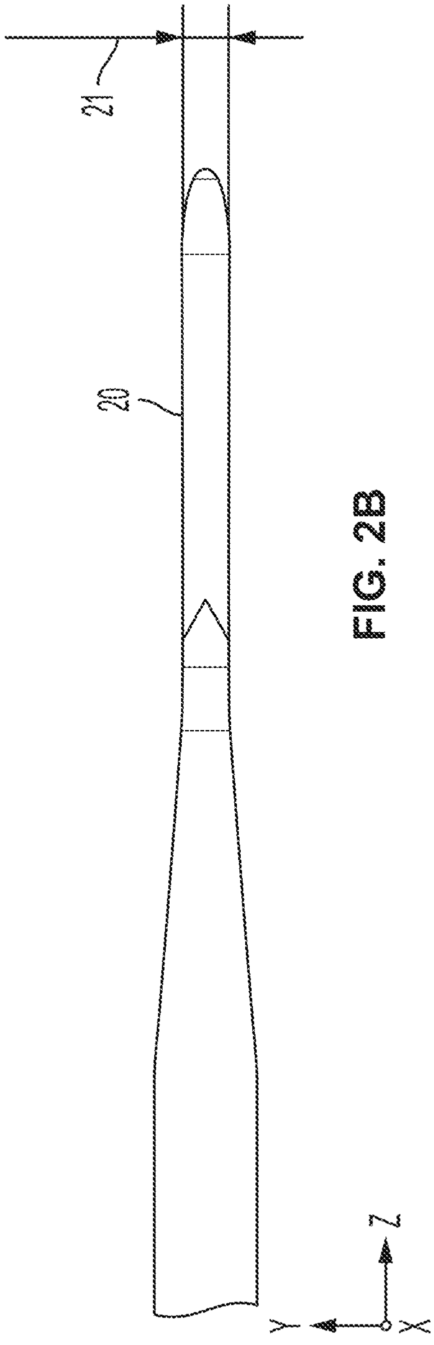

FIGS. 2A and 2B (collectively referred to as "FIG. 2") are an enlarged side view and bottom view, respectively, of cutting head 14 of cutting instrument 10 from FIGS. 1A and 1B. FIG. 2 illustrates cutting head 14 including cutting surface 22 defining a leading cutting edge 26. Leading cutting edge 26 can define a distal-most edge of cutting surface 22 that contacts tissue being cut when in use. Cutting head 14 is also illustrated as including guiding projection 20, which projects outwardly in a distal direction relative to leading cutting edge 26. For example, guiding projection 20 may project outwardly relative to leading cutting edge 26 to a distal end 28, which can define the distal-most end of both cutting head 14 and cutting instrument 10.

By configuring cutting head 14 with an outwardly projecting guiding projection 20, the clinician can advance the guiding projection ahead of cutting surface 22 to isolate one or more regions of soft tissue (e.g., ligaments) from adjacent tissue structure using the guiding projection. For example, the clinician can advance the distal end 28 of guiding projection 20 under one or more regions of soft tissue targeted for cutting, e.g., by inserting the guiding projection under one region of soft tissue targeted for cutting and over an adjacent region not intended to be cut, thereby capturing and/or segregating a targeted region of tissue from adjacent region. Cutting surface 22 trails the distal or leading end of guiding projection 20. As a result, tissue that is initially segregated from adjacent tissue by controlling the positioning of guiding projection 20 can subsequently be cut by cutting surface 22 by continuing to advance the cutting instrument forward, causing leading cutting edge 26 to contact and cut the tissue captured by the guiding projection.

In general, guiding projection 20 may extend outwardly from cutting surface 22 a distance sufficient to allow the clinician to segregate target tissue during use. However, the length guiding projection 20 extends past cutting surface 22 may desirably be limited so that target tissue captured by the guiding projection is positioned sufficiently close to the cutting surface to be readily cut without making manipulation of the cutting instrument challenging. Leading cutting edge 26 can be offset (e.g., setback) a distance 30 from the distal end 28 of guiding projection 20, which can be measured from the distal end of the guiding projection to the distal most location on the cutting edge. Distance 30 may be at least 1 mm, such as at least 3 mm, at least 5 mm, at least 7 mm, at least 9 mm, at least 11 mm, or at least 13 mm. Additionally or alternatively, distance 30 may be less than 25 mm, such as less than to 20 mm, less than 15 mm, or less than 10 mm. For example, distance 30 may range from 1 mm to 20 mm, such as from 5 mm to 15 mm, from 7 mm to 10 mm, or from 8 mm to 10 mm. For example, distance 30 may be approximately 9 mm (e.g., ±10%).

The distance 30 may be comparatively large relative to the overall length 32 of cutting head 14 (e.g., in the Z-direction indicated on FIG. 2). For example, a ratio of the length 32 of cutting head 14 divided by the distance 30 may be less than 5.0, such as less than 4.0, less than 3.5, or less than 3.0. In some implementations, the ratio of the length 32 of cutting head 14 divided by the distance 30 ranges from 2.0 to 3.5, such as from 2.5 to 2.75.

Guiding projection 20 can define any cross-sectional shape (e.g., in the X-Y plane), including polygonal shape (e.g., square, rectangle, hexagon), arcuate shape (e.g., circle, oval), and/or combinations of polygonal and arcuate shapes. Further, the cross-sectional shape of guiding projection 20 may be the same along the entire length of the guiding projection or may vary over the length of the guiding projection. In the illustrated example of FIG. 2, guiding projection 20 is shown as defining a cylindrical cross-sectional shape along at least a portion of its length.

Guiding projection 20 may be sized to be inserted under and/or between small dimensioned soft tissue, allowing the clinician to segregate one or more regions of soft tissue to be cut from adjacent regions of soft tissue not to be cut. Accordingly, guiding projection 20 may typically have a comparatively small cross-sectional size. In some implementations, guiding projection 20 has a major cross-sectional dimension 21 (e.g., diameter) less than or equal to 5 mm, such as less than or equal to 4 mm, less than or equal to 3 mm, less than or equal to 2 mm, or less than or equal to 1 mm. Guiding projection 20 can define the same size over the entirety of its length, or at least one portion of guiding projection 20 may have a different size (e.g., smaller size) that at least one other portion of the guiding projection. For example, in the configuration of FIG. 2, guiding projection 20 is illustrated as having a taper region 34 adjacent the distal-most end 28 of the guiding projection. When so configured, the cross-sectional size of guiding projection 20 may reduce moving from a proximal region of the guiding projection toward a distal region of the guiding projection. This can help provide a tapered distal end 28, which may be useful to guide guiding projection 20 under and/or between regions of soft tissue.

In some configurations, guiding projection 20 terminates in an apex or sharp point at distal end 28. In other configurations, guiding projection 20 terminates in a blunt distal end 28. For example, distal end 28 of guiding projection 20 may define a distal end 28 that is not pointed but rather defines an extent of surface area (e.g., in the X-Y plane indicated on FIG. 2). Configuring guiding projection 20 with a blunt distal end 28 may be useful to help prevent guiding projection 20 from piercing and/or cutting into tissue as the guiding projection is guided under one or more target regions of soft tissue of interest.

In general, cutting head 14 of cutting instrument 10 can define length 32 extending from a proximal end to the distal end 28 of the cutting head. Cutting head 14 can also define a width (e.g., in the X-direction indicated on FIG. 2) extending perpendicular to the length of the cutting head and the material thickness of the cutting head. For example, cutting head 14 can define a width extending from a first side edge 36A to a second side edge 36B. Cutting head 14 can further define a thickness (e.g., in the Y-direction indicated on FIG. 2) extending perpendicular to both the length and width of the cutting head.

Guiding projection 20 can be located at a number of different positions across the width of cutting head 14. In some examples, guiding projection 20 forms a side edge of cutting head 14. For example, guiding projection 20 may form a second side edge 36B of cutting head 14. Upon insertion of cutting head 14 into a body structure of a patient, second side edge 36B maybe oriented is a top edge of the cutting head, a bottom edge of the cutting head, and/or oriented in yet another direction in three-dimensional space. In other configurations, guiding projection 20 may be located elsewhere along the width of the cutting head between first side edge 36A and second side edge 36B.

In configurations where guiding projection 20 defines one side edge of cutting head 14 and/or bounds one side of cutting surface 22, the other side edge of the cutting head can have a variety of different configurations. In one example, cutting surface 22 forms the opposite side edge of the cutting head from guiding projection 20. In this configuration, the widthwise side edge of the cutting head may or may not be sharpened to provide a cutting edge extending along the widthwise side edge opposite guiding projection 20. In other examples, cutting head 14 includes a rail 38 defining first side edge 36A of the cutting head. When so configured, cutting surface 22 may be provided in the intermediate region between guiding projection 20 and rail 38.

Rail 38 may be a structure configured to slide against tissue placed in contact with the rail, e.g., without cutting the tissue. For example, rail 38 may define a non-cutting surface bounding cutting surface 22 on one side edge. Rail 38 can define any polygonal and/or arcuate cross-sectional shape (e.g., in the X-Y plane indicated on FIG. 2). Rail 38 can extend distally to a distal end 40. In some examples, distal end 40 of rail 38 is co-linear with at least a portion of leading cutting edge 26 of cutting surface 22. In other words, distal end 40 of rail 38 may be positioned so there is substantially no offset between at least a portion of leading cutting edge 26 (e.g., a portion immediately adjacent the rail) in the distal end of the rail. In other configurations, leading cutting edge 26 of cutting surface 22 may be offset (e.g., proximally or distally) the relative to the distal end 40 of rail 38.

For example, leading cutting edge 26 of cutting surface 22 may be recessed relative to distal end 40 of rail 38, e.g., in addition to being recessed relative to distal end 28 of guiding projection 20. When so configured, rail 38 may function as a second guiding projection in addition to guiding projection 20, albeit on an opposite side of the cutting head. In these implementations, rail 38 may have any of the configurations and offset dimensions discussed above with respect to guiding projection 20. In configurations in which leading cutting edge 26 of cutting surface 22 is recessed relative to the distal end 40 of rail 38, the cutting edge may be recessed the same distance or a different distance from the distal end of the rail compared to the distal end of guiding projection 20. For example, leading cutting edge 26 may be recessed a comparatively smaller distance from distal end 40 of rail 38 than the recessed distance 30 between distal end 28 of guiding projection 20 and a cutting surface. In some such examples, the distal-most location of leading cutting edge 26 is spaced a distance from the distal end 40 of rail 38 less than 7 mm, such as less than 5 mm less than 3 mm, or less than 2 mm.

In alternative configurations of cutting head 14, surfaces of guiding projection 20 and rail 38 facing each other may be taped to form opposed cutting edges (in addition to or in lieu of providing cutting surface 22). In one such configuration, guiding projection 20 and rail 38 may be movable relative to each other (e.g., about a pivot point to provide a scissor action) to cut tissue captured between the two surfaces. In the illustrated configuration, however, guiding projection 20 and rail 38 are located a fixed (non-movable) positions relative to each other.

Figure 2C:
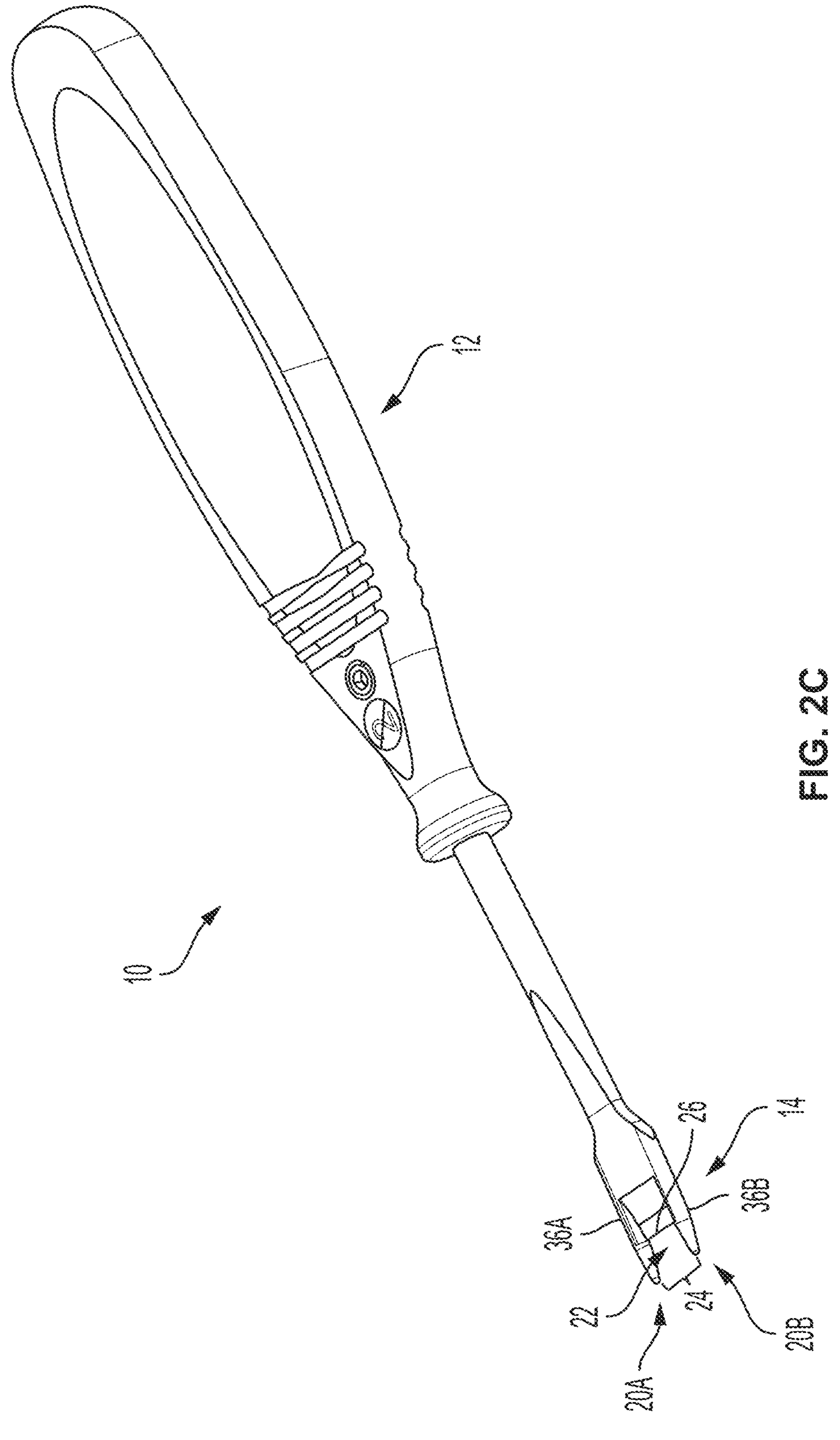
FIGS. 2C and 2D are perspective and top view illustrations, respectively, of an example configuration of a cutting instrument shown with a cutting head configured with two guiding projections.
Figure 2D:
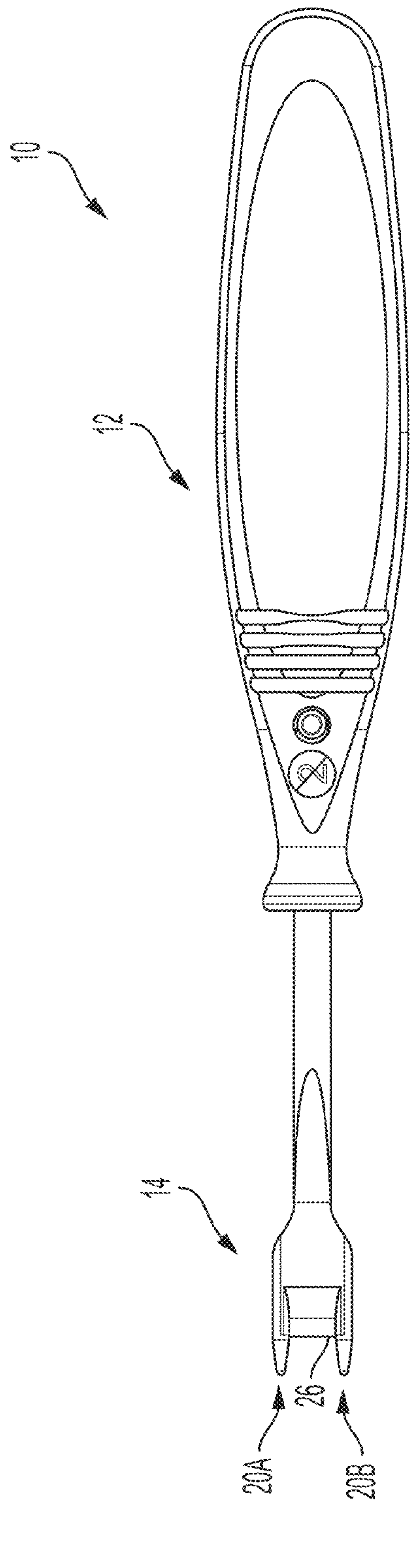

As noted, rail 38 may have any of the configurations and offset dimensions discussed above with respect to guiding projection 20. Accordingly, in some implementations, cutting head 14 of cutting instrument 10 may be configured with two guiding projections 20 bounding opposite side edges of cutting head 14. FIGS. 2C and 2D are perspective and top view illustrations, respectively, of cutting instrument 10 shown with cutting head 14 configured with a first guiding projection 20A and a second guiding projection 20B. Cutting head 14 including cutting surface 22 extending between first guiding projection 20A and second guiding projection 20B. When so configured, first guiding projection 20A can form first side edge 36A of cutting head 14, and second guiding projection 20B can form second side edge 36B of the cutting head.

Configuring cutting head 14 with two spaced-apart guiding projections 20A and 20B can be useful to help defined a bounded space between the two guiding projections that leading cutting edge 26 is recessed relative to. In use, the clinician can advance guiding projections 20A and 20B between the one or more ligaments to be cut and underlying soft tissue and/or bone. This can capture the targeted tissue (e.g., one or more ligaments) in notch 24 formed between first guiding projection 20A, second guiding projection 20B, and cutting surface 22. By offsetting cutting surface 22 relative to first guiding projection 20A and second guiding projection 20B, the two guiding projections can help the clinician navigate cutting head 14 relative to target tissue to be cut while providing non-cutting boundary structures on both sides of leading cutting edge 26, helping to prevent inadvertent cutting of tissue while navigating the cutting head.

First guiding projection 20A and second guiding projection 20B can each project outwardly in a distal direction relative to leading cutting edge 26. First guiding projection 20A and second guiding projection 20B can each have any of the configurations and dimensions discussed herein with respect to guiding projection 20. In the illustrated example of FIGS. 2C and 2D, first guiding projection 20A and second guiding projection 20B are shown as being symmetrically sized and shaped. That is, first guiding projection 20A and second guiding projection 20B each have the same size and shape. In other examples, first guiding projection 20A may be asymmetrically sized and/or shaped relative to second guiding projection 20B (e.g., such that first guiding projection 20A has a different size and/or shape than second guiding projection 20B).

With further reference to FIGS. 2A and 2B, cutting head 14 can define an intersection angle 42 between guiding projection 20 and cutting surface 22, indicating the angle at which the guiding projection extends relative to the cutting surface. In the illustrated example, intersection angle 42 is illustrated as being approximately 90°. In other examples, intersection angle 42 can be a different value. For example, intersection angle 42 may range from 45° to 135°, such as from 75° to 105°.

In general, cutting surface 22 of cutting head 14 may define a region of the cutting head having a reduced thickness compared to a remainder of the cutting head. The reduced thickness of the cutting surface may facilitate cutting as cutting head 14 is placed in contact with tissue to be cut. Cutting surface 22 may be formed by tapering the thickness of cutting head 14 in the region of the cutting surface (e.g., from a region of comparatively greater thickness toward the center of the cutting head to a region of comparatively lesser thickness at the outermost edge of the cutting surface). For example, with reference to FIG. 2, the thickness of cutting head 14 in the Y-direction indicated on the figure can be tapered over the region defining cutting surface 22.

In some implementations, cutting head 14 defines cutting surface 22 on a single side of the cutting head. With reference to FIG. 1B, for example, a first planar surface 44A can be defined by the length and width of cutting head 14 on one side of the cutting head, and a second planar surface 44B can be defined by the length and width of cutting head 14 on the opposite side of the cutting head. Cutting surface 22 can extend at an angle across the thickness of the cutting head (e.g., in the Y-direction indicated on FIG. 1B) toward the opposite planar surface.

In some examples, cutting head 14 defines cutting surfaces extending in a single direction across the thickness of the cutting head (e.g., from first plane 44A toward second plane 44B in the negative Y-direction), without having an opposed cutting surface extend in the opposite direction (e.g., from second plane 44B toward first plane 44A in the positive Y-direction). In these configurations, cutting surface 22 may be defined on the first planar side 44A of cutting head 14, and the second planar side 44B of the cutting head may be devoid of cutting surfaces. This configuration may be referred to as a single-sided taper configuration.

In other configurations, however, cutting head 14 may define cutting surfaces on both sides of the cutting head. For example, cutting head 14 may include a first cutting surface 22 tapered in a first direction across the thickness of the cutting head (e.g., from first plane 44A toward second plane 44B in the negative Y-direction) and a second cutting surface taped in a second direction across the thickness of the cutting head (e.g., from second plane 44B toward first plane 44A in the positive Y-direction). The two sets of cutting surfaces may intersect each other at a location between first plane 44A and second plane 44B, e.g., at a location that is substantially centered across the thickness of the cutting head, to define leading cutting edge 26. This configuration may be referred to as a dual-sided taper configuration.

The specific angle at which cutting surface 22 of cutting head 14 tapers towards leading cutting edge 26 can vary, e.g., based on the size and configuration of the cutting head. With reference to FIG. 1B, cutting head 14 can define a taper angle 46, which is the angle at which a cutting surface tapers across the thickness of the cutting head. In some examples, taper angle 46 may range from 5 degrees to 45 degrees, such as from 5 degrees to 25 degrees, or from 10 degrees to 20 degrees. When configured with cutting surfaces on both sides of cutting head 14, the two surfaces may taper toward each other at the same angle or at different angles.

In some examples, cutting surface 22 tapers at a single taper angle 46 across the entire cutting surface. In other configurations, cutting surface 22 tapers at multiple different angles across the cutting surface. For example, as seen in FIG. 1B, cutting surface 22 may define a first taper region having first taper angle 46 and a second taper region having a second taper angle 48. Second taper angle 48 may be different than first taper angle 46 (e.g., greater or less than the first taper angle). In the illustrated example, the region defining second taper angle 48 is positioned proximally or rearward of the region defining the first taper angle 46. Further, in this example, second taper angle 48 is illustrated as being smaller or shallower than first taper angle 46. In general, configuring cutting surface 22 with one or more tapered services can be beneficial to ease cutting of targeted soft tissue. Depending on the overall thickness of cutting head 14, cutting surface 22 may be a leading region of the cutting head that is not tapered relative to a remainder of the cutting head. These implementations may be used, for example, when the overall thickness of the cutting head is comparatively small such that a non-tapered cutting surface 22 still provides sufficient cutting of targeted soft tissue.

With further reference to FIG. 2A, leading cutting edge 26 of cutting surface 22 may extend straight across the width of the cutting head (e.g., in the X-direction indicated on the figure) or may define a curvature. In the illustrated configuration, leading cutting edge 26 of cutting surface 22 defines a curvature along the width of the cutting head, which is illustrated as a convex curvature in which a middle or intermediate region of the leading cutting surface is recessed proximally relative to regions of the leading cutting edge adjacent the side edges. In other examples, leading cutting edge 26 of cutting surface 22 may define a convex curvature in which a middle or intermediate region of the leading cutting surface extends distally outwardly relative to regions of the leading cutting edge adjacent the side edges. In still other configurations, leading cutting edge 26 may angle proximally or distally from first side edge 36A to a second side edge 36B.

The specific dimensions of cutting instrument 10, including cutting head 14, can vary depending on the desired application. In some implementations, the longitudinal length 32 of cutting head 14 may range from 5 mm to 50 mm, such as from 10 mm to 35 mm, or from 20 mm to 30 mm. The width 50 of cutting head 14 between first side edge 36A and second side edge 36B may range from 5 mm to 13 mm, such as from 6 mm to 10 mm, or approximately 8 mm (e.g., ±10%). Depending on the configuration, the width 52 of cutting surface 22 (defining a length of leading cutting edge 26), may be less than the overall width of the cutting head, such as at least 1 mm less, at least 2 mm less, or at least 3 mm less. For example, the width 52 of cutting head 14 finding cutting surface 22 may range from 2 mm to 10 mm, such as from 3 mm to 7 mm, or approximately 5 mm (e.g., ±10%). In some implementations, a maximum thickness of cutting head 14 ranges from 0.5 mm to 4 mm, such as from 1 mm to 3 mm, or approximately 2 mm (e.g., ±10 percent).

In general, cutting instrument 10, including handle 12 and cutting head 14, can be formed of any desired material or combinations of materials. Typically, cutting head 14 will be fabricated of metal to form a sharp cutting surface, such as steel (e.g., stainless steel), titanium, or the like, although may be formed of ceramic or other sharpenable materials. Handle 12 may be formed of a variety of materials, including one or more metals and/or polymeric materials.

In some configurations, handle 12 and cutting head 14 are formed as a unitary structure (e.g., via casting, milling) defined by a single type of material. In other configurations, handle 12 and cutting head 14 may be formed as separate structures joined together to couple the cutting head to the handle for subsequent use. In some such configurations, handle 12 may be formed of a different material (e.g., a polymeric material) then cutting head 14 (which may be formed of metal material), e.g., for increased grip ability and/or comfort and holding. For example, handle 12 may define a receiving cavity at second and 18, and an end of cutting head 14 opposite leading cutting edge 26 can be inserted into the receiving cavity to interconnect the handling cutting head. Fixation means (e.g., adhesive, screws, bolts, welding) may be used to permanently affix the cutting head to the handle. In other configurations, cutting head 14 may be detachably attached to handle 12 to allow the handle to be used with different interchangeable cutting heads (e.g., each having the same configuration or having different configurations from each other).

Handle 12 may generally be configured to be gripped manually by the hand of a clinician using cutting instrument 10. Handle 12 may have an enlarged cross-sectional size (e.g., width, thickness) relative to cutting head 14 to provide a larger surface for grasping. In some configurations, handle 12 includes surface texturing, such as knobs, ribs, knurls, and/or other features that facilitate gripping of the handle without slippage. While handle 12 may generally be designed to be gripped manually by the hand of the clinician, in other configurations, handle 12 may be designed to be inserted into a powered hand instrument that can drive movement of cutting head 14 via the handle. Handle 12 can have any desired length between first end 16 and second end 18 although, in some examples, may exhibit a length ranging from 50 mm to 200 mm, such as from 100 mm to 150 mm.

In the illustrated arrangement of FIGS. 1A, 1B, 2A, and 2B, handle 12 is illustrated as extending co-linearly with cutting head 14. That is, the longitudinal axis defined by handle 12 is illustrated as extending co-linearly with the longitudinal axis defined by cutting head 14 (e.g., in the X-Z plane indicated on FIG. 1A and in the Y-Z plane indicated on FIG. 2B). In other configurations, handle 12 (the entire handle or portion thereof) may be offset from and/or angled relative to the longitudinal axis defined by cutting head 14.

Figure 2E:
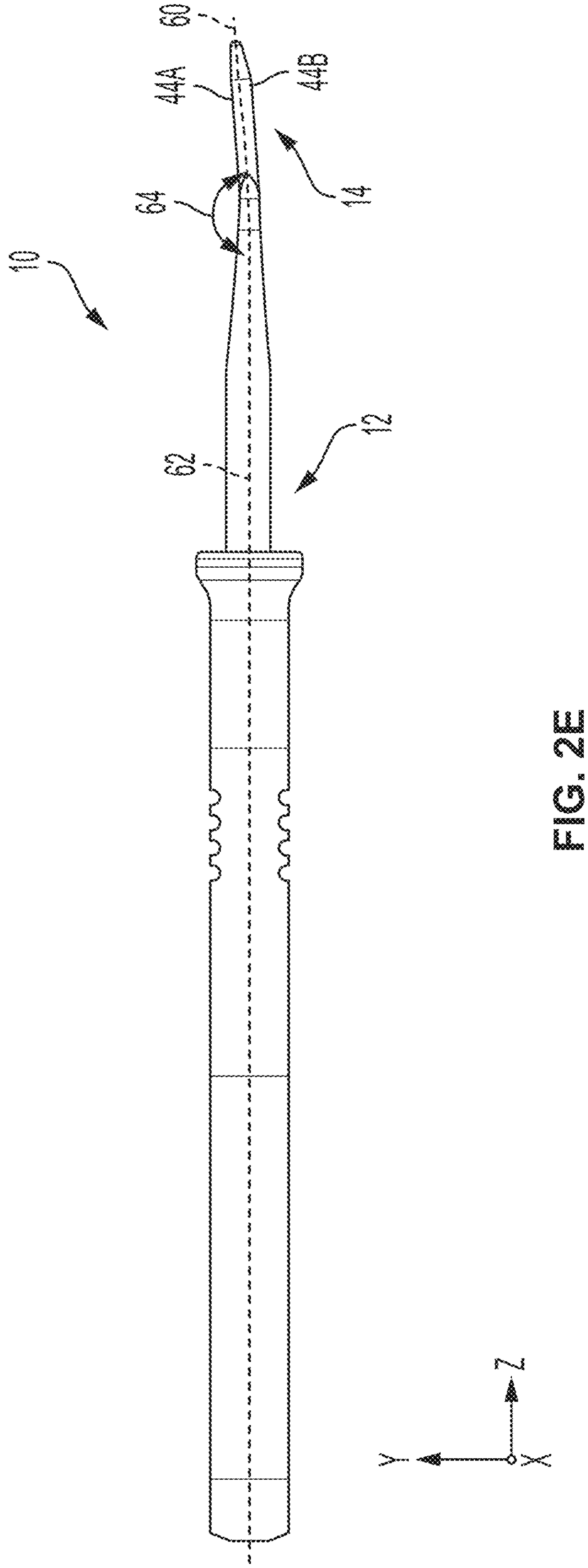
FIG. 2E is a side view of the cutting instrument of FIGS. 1A and 1B showing an example configuration where the cutting head is angled relative to the handle.

For example, FIG. 2E is a side view of cutting instrument 10 showing an example configuration where cutting head 14 is angled relative to handle 12. When so configured, a longitudinal axis 60 defined by cutting head 14 may be angled relative to a longitudinal axis 62 defined by handle 12 to define an angle 64 between the two axes. Cutting head 14 may be angled in a direction that causes first planar surface 44A and/or second planar surface 44B to be positioned out of plane with handle 12 (e.g., in the X-Z plane indicated on FIG. 2E). In some examples, angle 64 may be within a range from 5 degrees and 45 degrees, such as from 10 degrees to 25 degrees. Angle 64 may be defined by a sharp transition or angular intersection between handle 12 and cutting head 14. Alternatively, instrument 10 may define a radius of curvature between handle 12 and cutting head 14 that defines angle 64. Configuring cutting instrument 10 with an angular offset between handle 12 and cutting head 14 may be useful to help the clinician guide cutting instrument 10 into an incision location and/or to target tissue to be cut using the instrument.

With further reference to FIGS. 1 and 2, in configurations where handle 12 and cutting head 14 are formed as a unitary body and there is not an otherwise distinguishing transition between the handling cutting head, handle 12 may be deemed to have an arbitrary second end 18 between the handle and cutting head 14 where the handle transitions into the cutting head without distinguishing size or shape change between the handle and the cutting head.

As briefly discussed above, cutting instrument 10 can be used during a variety of different procedures, including as part of a bone alignment procedure. In some examples, cutting instrument 10 is utilized during a procedure in which one or more bones of the foot are realigned. To further understand such example techniques, the anatomy of the foot will be described with respect to FIGS. 4A and 4B. A bone misalignment in the foot may be caused by metatarsus adductus, hallux valgus (bunion), arthritis, and/or other condition. The condition may present with a misalignment of one or more bones in the foot.

Figure 3B:
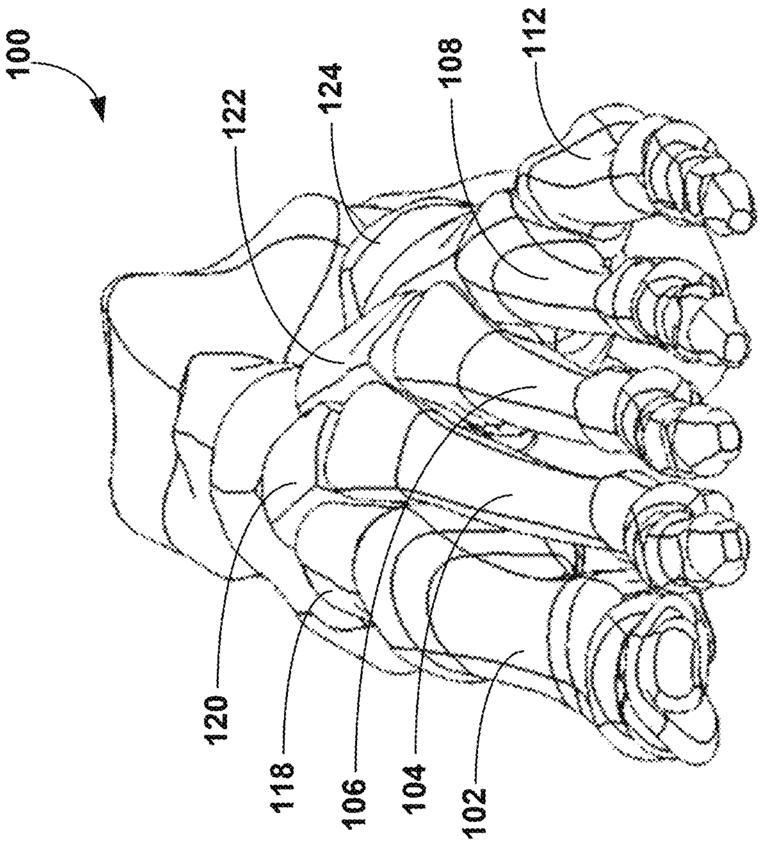
FIGS. 3A and 3B are top and front views, respectively, of a foot showing example normal metatarsal alignment positions
Figure 3A:
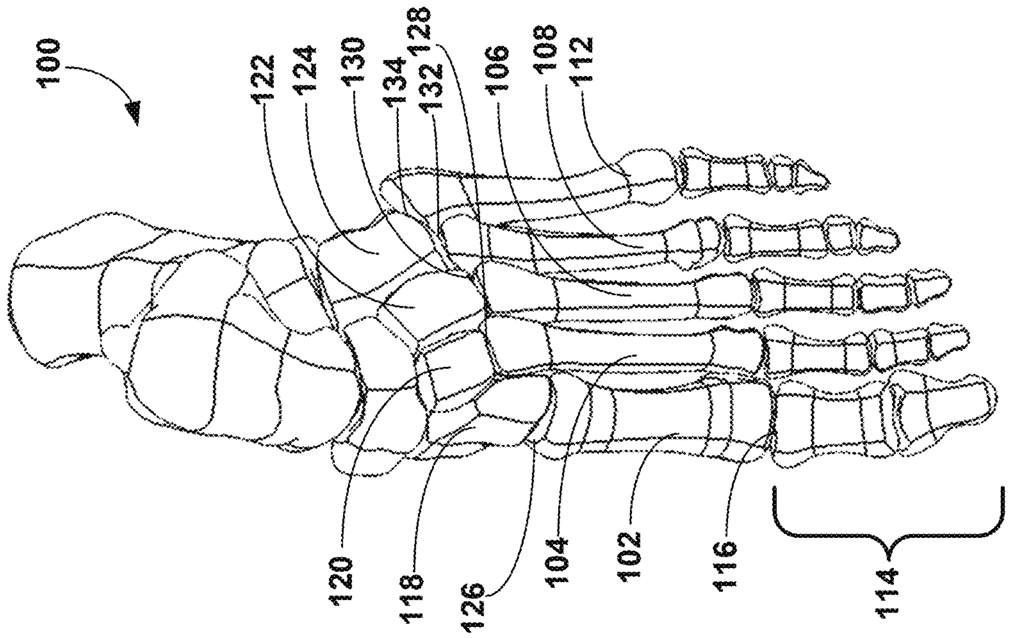

FIGS. 3A and 3B are top and front views, respectively, of a foot 100 showing normal metatarsal alignment positions. Foot 100 is composed of multiple bones including a first metatarsal 102, a second metatarsal 104, a third metatarsal 106, a fourth metatarsal 108, and a fifth metatarsal 112. First metatarsal 102 is on a medial-most side of the foot while fifth metatarsal 112 is on a lateral-most side of the foot. The metatarsals are connected distally to phalanges 114 and, more particularly, each to a respective proximal phalanx. The joint 116 between a metatarsal and a corresponding opposed proximal phalanx is referred to as a metatarsophalangeal ("MTP") joint. The first MTP joint is labeled as joint 116 in FIG. 1A, although second, third, fourth, and fifth MTP joints are also illustrated in series adjacent to the first MTP joint.

The first metatarsal 102 is connected proximally to a medial cuneiform 118, while the second metatarsal 104 is connected proximally to an intermediate cuneiform 120, and the third metatarsal 106 is connected proximally to lateral cuneiform 122. The fourth and fifth metatarsals 108, 112 are connected proximally to the cuboid bone 124. The joint between a metatarsal and opposed bone (cuneiform, cuboid)

is referred to as the tarsometatarsal ("TMT") joint. FIG. 4A designates a first TMT joint 126, a second TMT joint 128, a third TMT joint 130, a fourth TMT joint 132, and a fifth TMT joint 134. The angle between adjacent metatarsals is referred to as the intermetatarsal angle ("IMA").

In the example of FIGS. 3A and 3B, foot 100 is illustrated as having generally normally aligned metatarsals. Normal metatarsal alignment may be characterized, among other attributes, by a low intermetatarsal angle (e.g., 9 degrees or less, such as 5 degrees or less) between the first metatarsal and the second metatarsal. In addition, the lesser metatarsals may be generally parallel to a longitudinal axis bisecting the foot proximally to distally.

Figure 4:
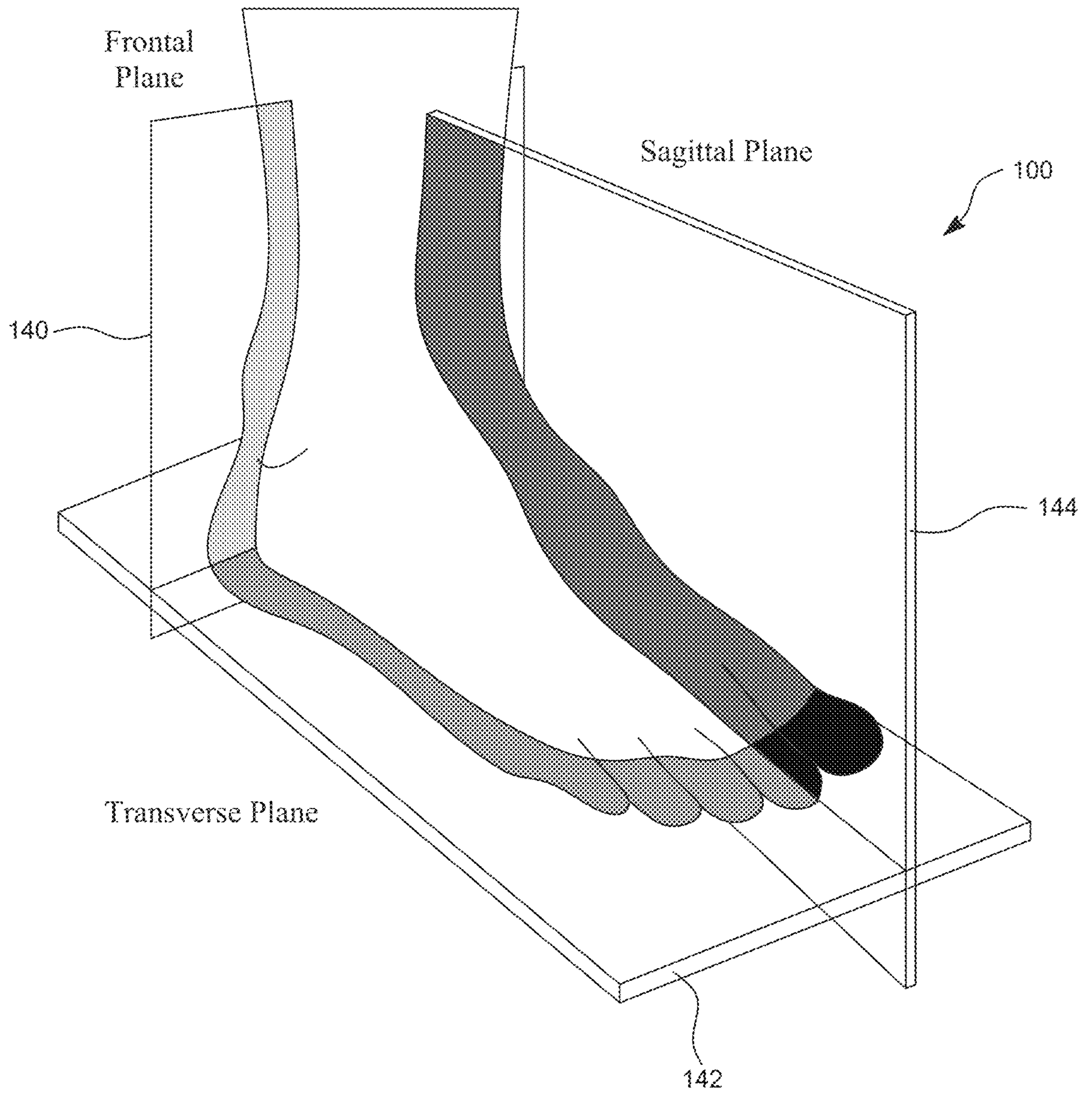
FIG. 4 illustrates the different anatomical planes of the foot.

FIG. 4 illustrates the different anatomical planes of foot 100, including frontal plane 140, transverse plane 142, and sagittal plane 144. The frontal plane 140, which is also known as the coronal plane, is generally considered any vertical plane that divides the body into anterior and posterior sections. On foot 100, the frontal plane 140 is a plane that extends vertically and is perpendicular to an axis extending proximally to distally along the length of the foot. The transverse plane 142, which is also known as the horizontal plane, axial plane, or transaxial plane, is considered any plane that divides the body into superior and inferior parts. On foot 100, the transverse plane 142 is a plane that extends horizontally and is perpendicular to an axis extending dorsally to plantarly (top to bottom) across the foot. Further, the sagittal plane 144 is a plane parallel to the sagittal suture which divides the body into right and left halves. On foot 100, the sagittal plane 144 is a plane that extends vertically and intersects an axis extending proximally to distally along the length of the foot. For patients afflicted with certain bone misalignments, one or more of metatarsals may be deviated medially in the transverse plane (e.g., in addition to or in lieu of being rotated in the frontal plane and/or being deviated in the sagittal plane relative to clinically defined normal anatomical alignment for a standard patient population).

Figure 5:
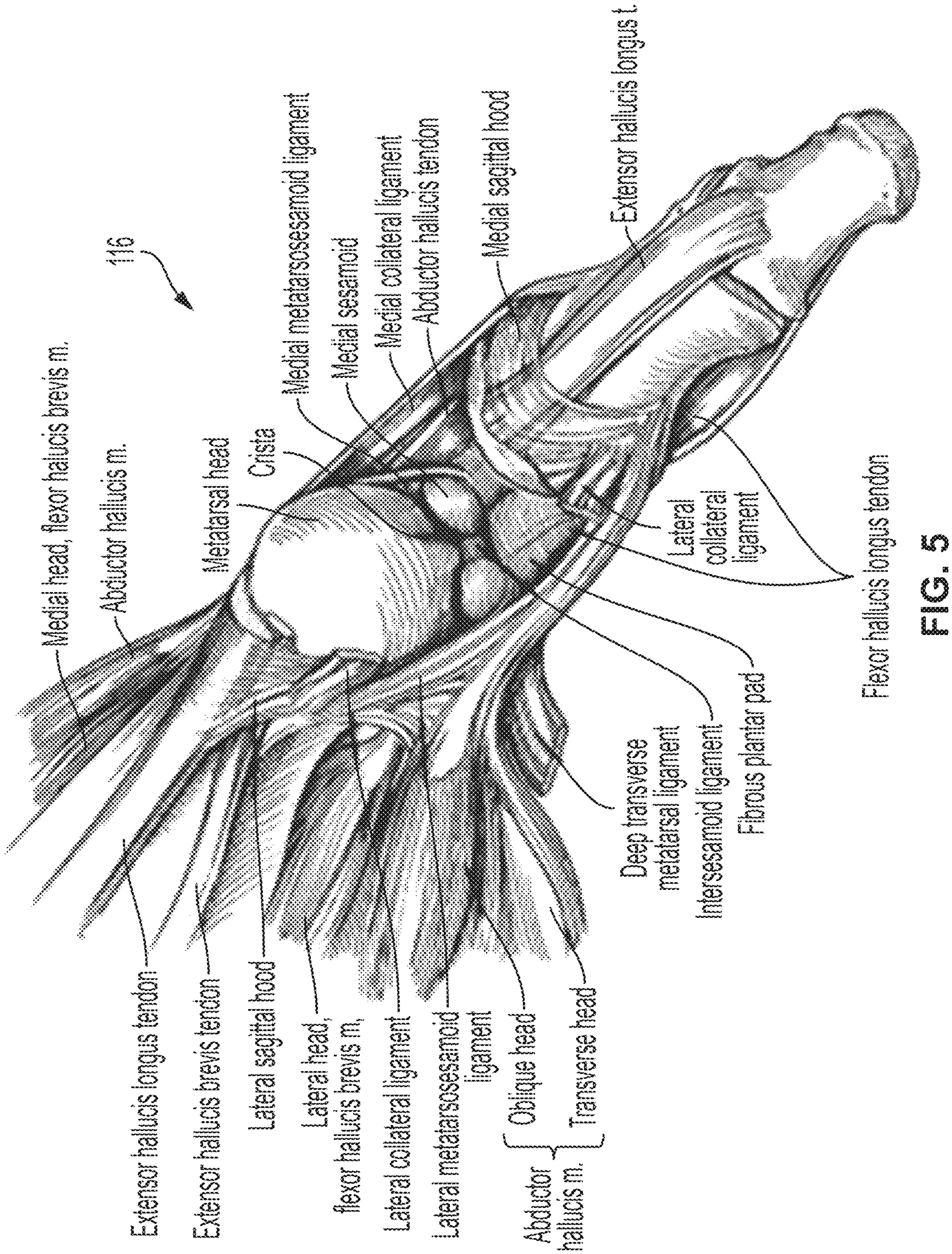
FIG. 5 is a superolateral view of the bone-ligament-capsular anatomy of the first MTP joint.

FIG. 5 is a superolateral view of the bone-ligament-capsular anatomy of the first MTP joint 116. As seen in FIG. 5, the first MTP joint 116 includes the distal head of the first metatarsal, the proximal head of the proximal phalanx, and the medial and lateral sesamoids. The sesamoid complex may be characterized as including two sesamoid bones, eight ligaments, and seven muscles. The sesamoid articulation with the first metatarsal head is in continuity with that of MTP articulation. Most of the capsuloligamentous stabilizing structures are concentrated on the plantar surface of the joint.

The dorsal surface of the MTP joint is dominated by the extensor hallucis longus tendon (EHL), which lies in the dorsal midline. The extensor hallucis brevis (EHB) tendon is just plantar and lateral to the EHL. The sagittal hood spreads out from the tendon sheath, encasing the ligaments to form a confluence of thickened capsular tissue extending plantarward to the collateral ligaments in the midline both medially and laterally. These capsuloligamentous structures generally align at the equator of the joint, extending from the upper condylar region of the first metatarsal head to the base of the proximal phalanx.

A small bony ridge or crista separates the two sesamoid bones as they lie in their respective grooves. A dense plantar pad covers the sesamoids and anchors them to the proximal phalanx. The medial sesamoid is ovoid and usually slightly more distal and larger than the lateral one. The sesamoids are encased by two heads of the flexor hallucis brevis tendons.

Figure 6A:
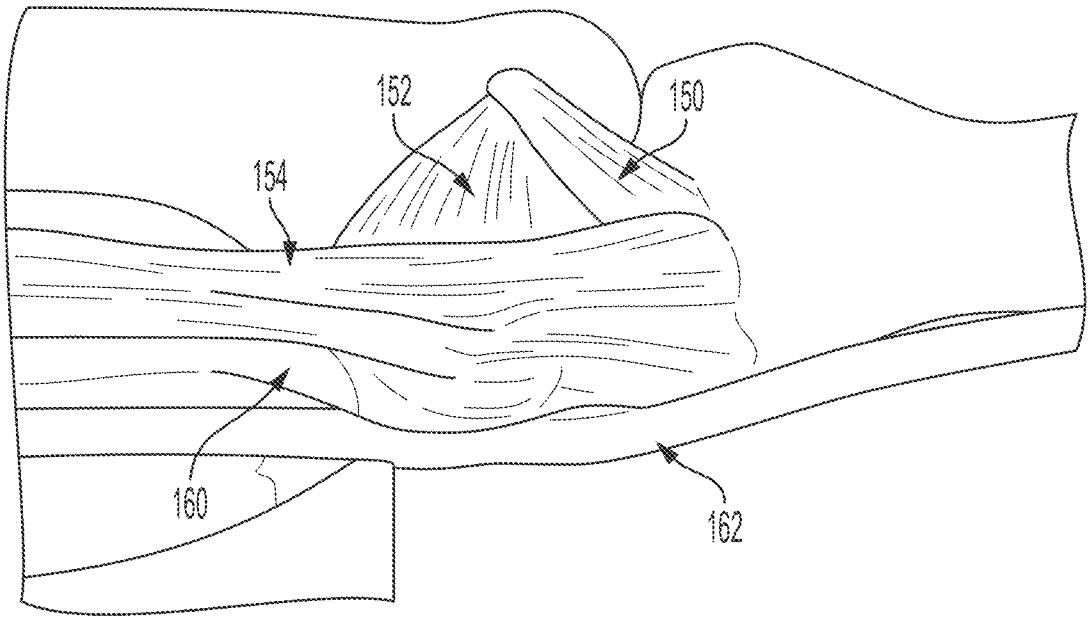
FIGS. 6A and 6B are medial and lateral views, respectively, of the first metatarsophalangeal (MTP) joint with the extensor hood structures removed to depict certain structural elements of the plantar capsuloligamentous-sesamoid complex.
Figure 6B:
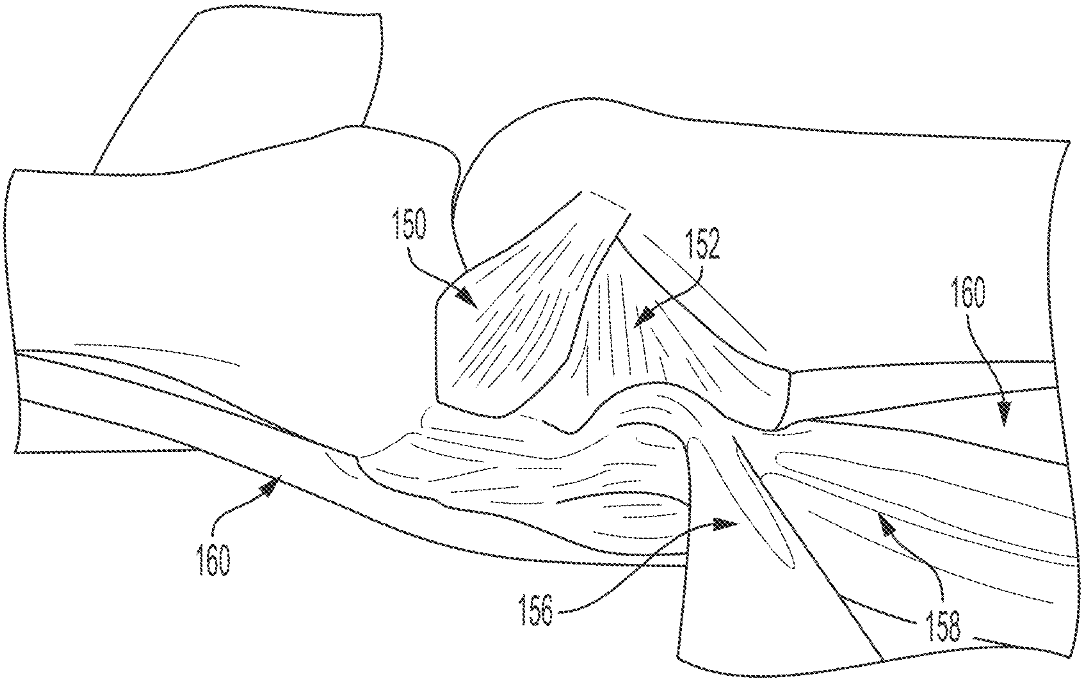

FIGS. 6A and 6B are medial and lateral views, respectively, of the first metatarsophalangeal (MTP) joint with the extensor hood structures removed to depict certain structural elements of the plantar capsuloligamentous-sesamoid complex. As illustrated, the collateral ligamentous complexes of the capsuloligamentous-sesamoid complex are found medially and laterally and include the main collateral ligament 150 and the accessory sesamoid ligaments 152. The abductor hallucis 154 tendon inserts on the medial sesamoid and blends with the capsular structures on the medial side of the joint. The transverse 156 and oblique 158 heads of the adductor hallucis muscle send fibers to the lateral sesamoid, capsule and plantar plate. The medial and lateral heads of the flexor hallucis brevis 160 insert on to the sesamoids found along the plantar surface of the metatarsal. The flexor hallucis longus tendon 162 is also depicted.

Figure 7:
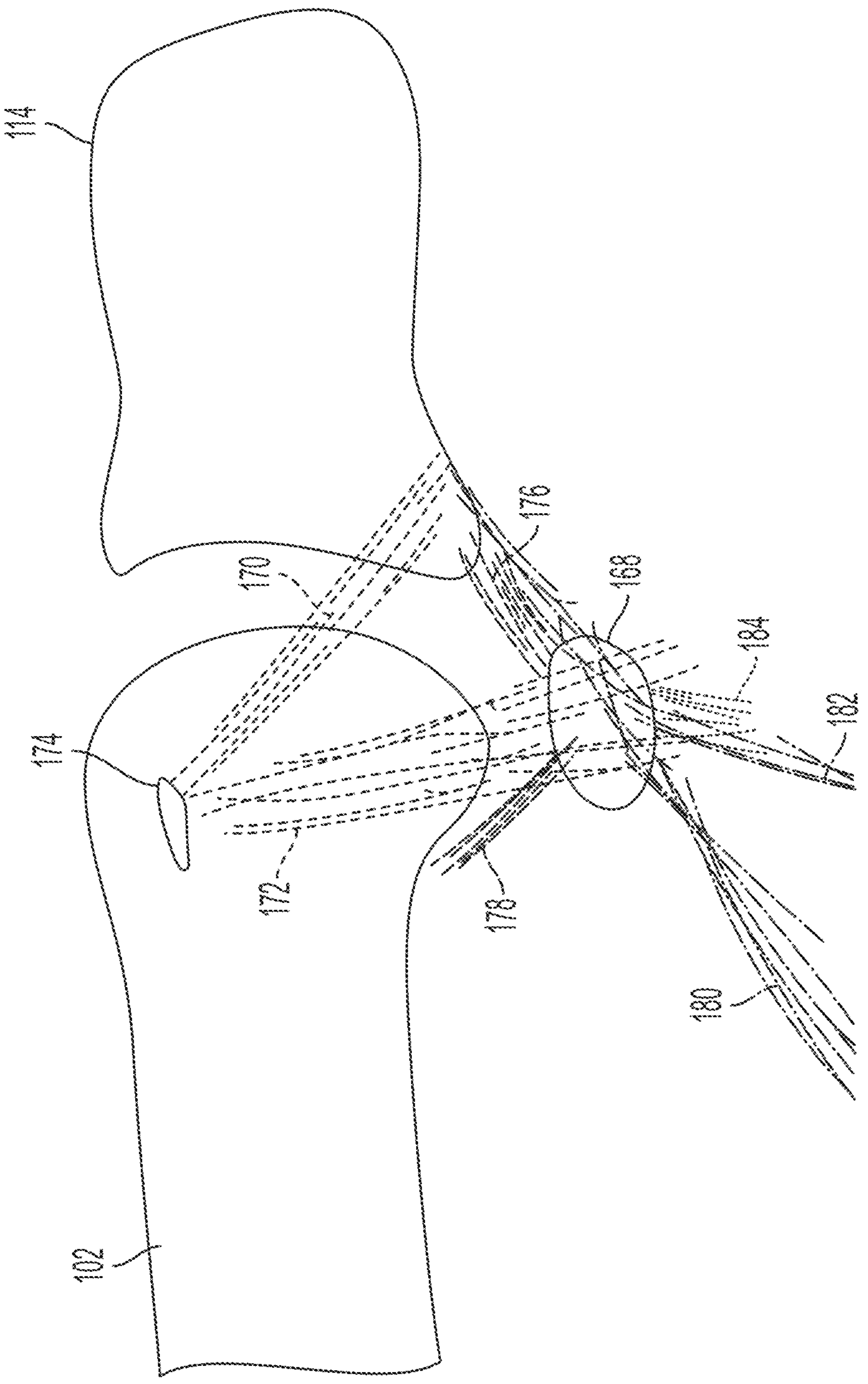
FIG. 7 is lateral side view of the first metatarsophalangeal (MTP) joint further illustrating soft tissue anatomy at the joint.

FIG. 7 is lateral side view of the first metatarsophalangeal (MTP) joint further illustrating soft tissue anatomy at the joint. As illustrated in FIG. 7, the first TMT is formed between the first metatarsal 102 and proximal phalanx 114, with lateral sesamoid 168 positioned under the joint. A lateral metatarsophalangeal ligament 170, which is also referred to as a proper collateral ligament, is illustrated as extending from the lateral epicondyle 174 to the proximal phalanx. A lateral supervisory ligament 172, which is also referred to as an accessory collateral ligament, is illustrated as extending from lateral epicondyle 174 to lateral sesamoid 168. A lateral phalangeal-sesamoid ligament 176 is illustrated as extending from lateral sesamoid 168 to proximal phalanx 114. A lateral metatarsosesamoid ligament is illustrated as extending from lateral sesamoid 168 to first metatarsal 102. Also illustrated in FIG. 7 are the oblique head adductor 180, the transverse adductor head 182, and the deep transverse metatarsal ligament 184.

Figure 8:
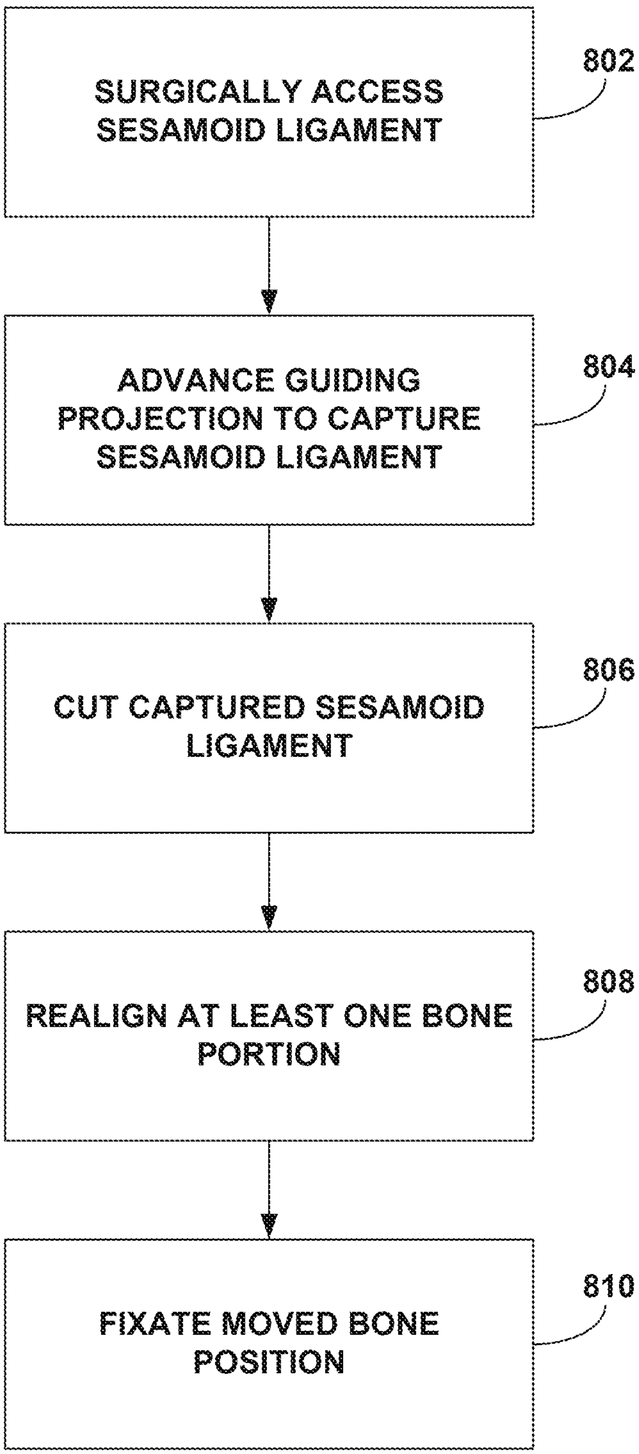
FIG. 8 is a flow diagram of an example bone realignment technique that can be performed utilizing a cutting instrument according to the disclosure.

Cutting head 14 can be used as part of a technique to cut soft tissue, such as one or more ligaments and/or muscles illustrated and/or discussed with respect to FIGS. 5-7 to help mobilize a bone (e.g., first metatarsal 102) for realignment. FIG. 8 is a flow diagram of an example bone realignment technique that can be performed utilizing a cutting instrument 10 according to the disclosure. As will be described, in some examples of the technique of FIG. 8, cutting instrument 10 may be utilized to cut soft tissue on the lateral side of first metatarsal 102 to help mobilize a bone for subsequent bone realignment.

Example cutting steps utilizing cutting instrument 10 that can be performed will be described with reference to FIG. 8. Additional details on example surgical techniques, including example instrumentation that can be used during the techniques, can be found in U.S. Pat. No. 9,622,805, issued Apr. 18, 2017 and entitled "BONE POSITIONING AND PREPARING GUIDE SYSTEMS AND METHODS," US Patent Publication No. 2020/0015856, published Jan. 16, 2020 and entitled "COMPRESSOR-DISTRACTOR FOR ANGULARLY REALIGNING BONE PORTIONS," and US Patent Publication No. 2021/0361330, published Nov. 25, 2021 and entitled "DEVICES AND TECHNIQUES FOR TREATING METATARSUS ADDUCTUS," the entire contents of each of which are incorporated herein by reference.

Figure 10:
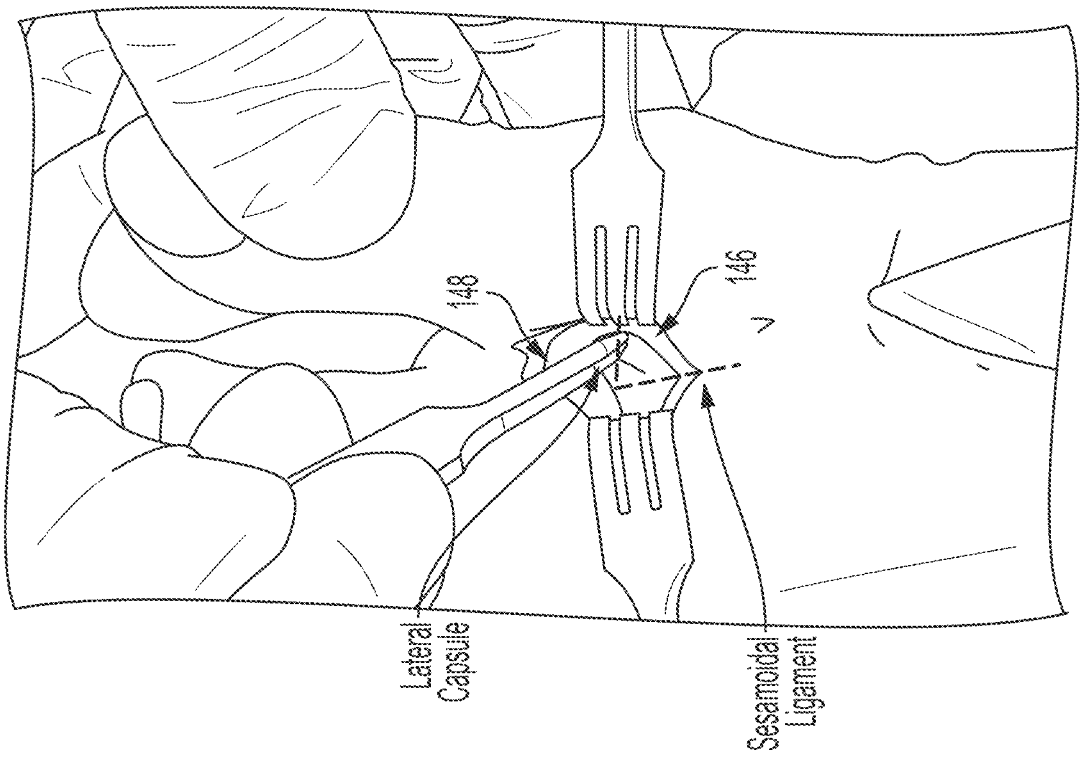
FIGS. 9 and 10 are dorsal views of a foot illustrating example incision locations on the lateral side of the MTP joint capsule for accessing underlying sesamoidal ligaments.
Figure 9:
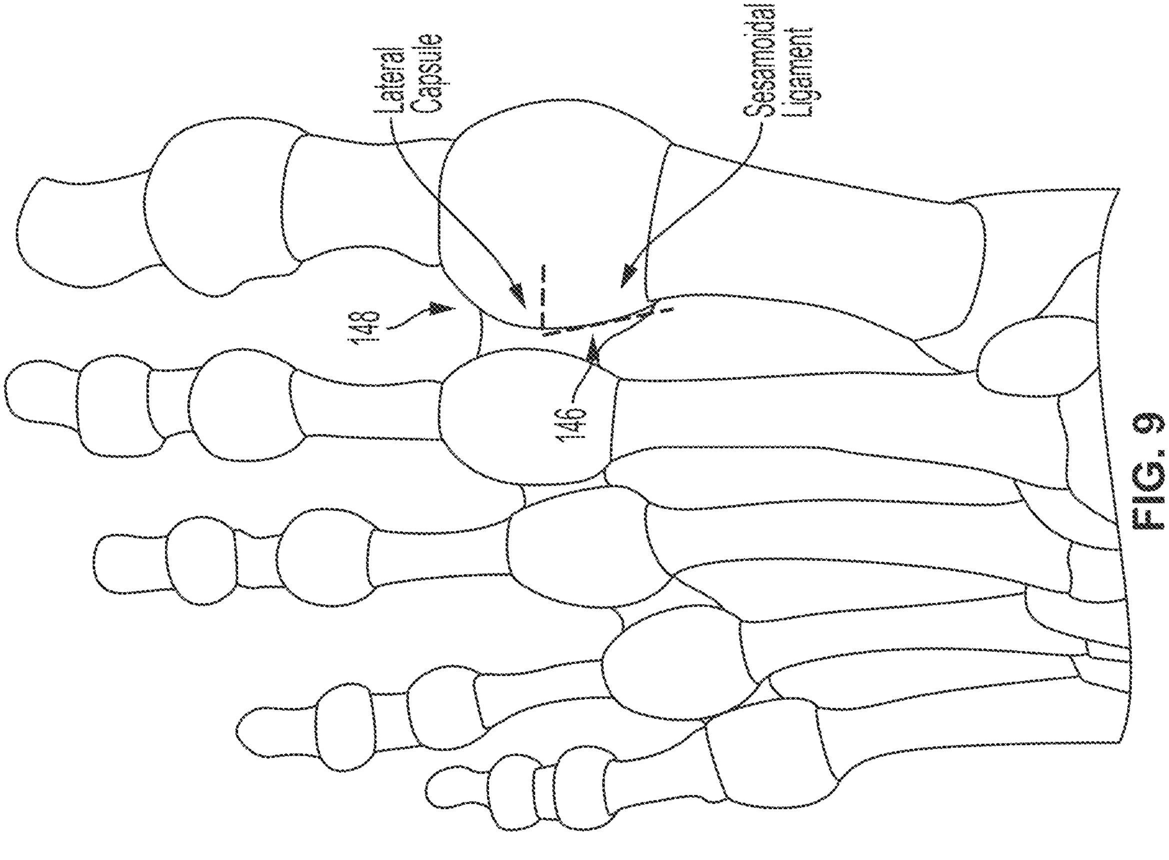

The example technique of FIG. 8 includes making an incision through the skin of the patient to surgically access soft tissue to be cut, such as a one or more sesamoidal ligaments in the foot (802). The incision can be made through the skin, such as on a dorsal side of the foot, to access a MTP joint and/or an intermetatarsal joint space between adjacent metatarsals. For example, the incision may be made from a dorsal side of the foot by cutting into a first metatarsophalangeal joint capsule. The clinician may cut into a lateral side of the first metatarsophalangeal joint capsule, e.g., from a dorsal side of the foot. The cut may be positioned and made to a depth sufficient to expose underlined soft tissue (e.g., ligaments) subsequently targeted for cutting during the procedure. The clinician may use a scalpel or other bladed cutting instrument to perform the access cut. FIGS. 9 and 10 are dorsal views of foot 100 illustrating example incision locations 146 on the lateral side of the MTP joint capsule 148 for accessing underlying lateral sesamoidal ligaments. As shown in these examples, the example incisions locations 146 include a proximal-to-distal incision on the lateral side of the MTP joint capsule 148 and/or a medial-to-lateral incision (e.g., intersecting the proximal-to-distal incision) extending from the lateral side of the MTP joint capsule 148 medially into the capsule.

With further reference to FIG. 8, the example technique involves advancing guiding projection 20 of cutting instrument 10 into the access incision created through the skin of the patient and using the guiding projection to capture one or more target regions of soft tissue to be cut (804). For example, the clinician can introduce cutting head 14 of cutting instrument 10 into the incision created in the lateral side of the MTP joint capsule. The clinician can advance guiding projection 20 (followed by remainder of cutting head 14) to the target soft tissue, e.g., by advancing the cutting head plantarly into the incision and/or proximally up the intermetatarsal space and/or distally down the metatarsal space.

Independent of the specific direction of movement, the clinician can use guiding projection 20 to separate one or more regions of soft tissue targeted for cutting from one or more adjacent regions of soft tissue not intended to be cut. For example, the clinician can guide distal end 28 of guiding projection 20 under one or more ligaments and/or muscles, capturing the ligaments and/or muscles in the notch 24 between the guiding projection and cutting surface 22. This can position guiding projection 20 between the captured ligaments and/or muscles and underlying structure (e.g., soft tissue, bone). In some examples, the clinician can use first guiding projection 20A and second guiding projection 20B to separate one or more regions of soft tissue targeted for cutting from adjacent regions of soft tissue on opposite sides of the cutting head not intended to be cut. The clinician can guide the distal ends of first guiding projection 20A and second guiding projection 20B under one or more ligaments and/or muscles, capturing the ligaments and/or muscles in the notch 24 between the two guiding projections and cutting surface 22. It should be appreciated that reference to positioning the guiding projection under certain tissue does not require any specific orientation with respect to gravity but instead is intended to refer to positioning the guiding projection between targeted tissue and underlying matter.

The specific soft tissue targeted by the clinician for cutting may vary depending on the specific procedure being performed and extent of bone mobilization and release desired by the clinician. In some applications, the clinician advances guiding projection 20 of cutting instrument 10 under at least accessory supervisory ligament 172. Additionally or alternatively, the clinician can advance guiding projection 20 of cutting instrument 10 under proper collateral ligament 170. Yet further additionally or alternatively, the clinician may advance guiding projection 20 of cutting instrument 10 under one or more of lateral metatarsophalangeal ligament 176, lateral sesamoid phalangeal ligament 178, oblique head adductor 180, transverse head adductor 182, and/or deep transverse metatarsal ligament 184. The clinician may capture one or more of the target regions of soft tissue in notch 24 at the same time, or may capture different target regions of soft tissue through different cutting passes.

With the one or more regions of soft tissue targeted for cutting segregated by guiding projection 20 and captured in notch 24, the clinician can proceed to use cutting surface 22 of cutting instrument 10 to cut the captured tissue (806). The clinician may further advance cutting instrument 10 in the direction the instrument was advanced to initially capture the soft tissue, causing leading cutting edge 26 of cutting surface 22 to contact and/or cut through the tissue captured in the notch.

For example, if the clinician initially advances guiding projection 20 of cutting instrument 10 in a first direction (e.g., a plantar direction, dorsal direction, proximal direction, distal direction, plantar-proximal direction, plantar-distal direction) to capture target soft tissue, the clinician may further advance the cutting instrument in that first direction to subsequently cut the captured soft tissue. In practice, the clinician may initially feel resistance to pushing as cutting surface 22 is bearing against the captured soft tissue, with the resistance diminishing or releasing when the cutting surface has completed cutting through the soft tissue. This may be accompanied by an audible sound, such as a popping sound, indicating the tissue has been cut.

In some examples, the clinician may advance cutting head 14 in one direction to capture and cut one or more regions of soft tissue (e.g., one or more ligaments, muscles) and then turn and advance the cutting head in a different direction to capture and cut one or more other regions of soft tissue. For example, the clinician may initially advance cutting head 14 in a generally proximal direction (e.g., to capture and cut at least accessory supervisory ligament 172 and proper collateral ligament 170) then subsequently turn cutting head 14 in a different direction, such as a generally distal direction (e.g., to capture and cut other soft tissue). The clinician may or may not make this turn and reverse movement without removing cutting head 14 from the incision. After performing any desired cutting, cutting instrument 10 may be removed for subsequent steps of the surgical procedure.

In the example technique of FIG. 8, the technique includes moving at least a portion of first metatarsal 102 in at least one plane (808). For example, before or after performing a soft tissue release using cutting instrument 10 as described above, at least a portion of first metatarsal 102 may be realigned in one or more planes. For example, at least a portion of the metatarsal can be moved in at least the transverse plane to close in intermetatarsal angle between the bone being moved in adjacent bone. Additionally or alternatively, at least a portion of the metatarsal may be moved in the frontal plane (e.g., to reposition the sesamoid bones substantially centered under the metatarsal). In some examples, the portion of the metatarsal can be moved in multiple planes, such as the transverse plane and/or frontal plane and/or sagittal plane (e.g., each of the transverse, frontal, and sagittal planes). The clinician may or may not utilize a bone positioning device to facilitate movement of the bone portion. The moved position of the metatarsal can result is realignment of the metatarsal relative to one of more other adjacent bones.

In some examples, such as during an osteotomy procedure, the clinician may realign a distal portion of the first metatarsal relative to adjacent proximal portion. In these applications, the clinician may surgically access the first metatarsal (e.g., make in incision through the skin of the patent) at a location between the TMT joint and MTP joint. The clinician may cut the first metatarsal to form a proximal portion extending back to the TMT joint and a distal portion extending to the MTP joint. The incision can be made through the skin, such as on a dorsal side of the foot, a medial side of the foot, on a dorsal-medial side of the foot, on a lateral side of the foot, or yet other location in the foot. The clinician can then realign the distal portion of the first metatarsal in one or more planes.

In other examples, the clinician may realign an entire length of the first metatarsal. In these examples, the clinician may make an incision to access the first TMT joint 126. Again, the incision can be made through the skin, such as on a dorsal side of the foot, a medial side of the foot, on a dorsal-medial side of the foot, on a lateral side of the foot, or yet other location in the foot. In either case, the clinician can prepare the end of the first metatarsal and the end of the medial cuneiform across the first TMT joint 126 for fusion. One or both of the end faces of the metatarsal and the opposed bone can be prepared before and/or after the metatarsal is moved relative to the cuneiform. Accordingly, unless otherwise specified, the order of bone preparation and/or movement is not limited.

In general, the clinician can prepare the end of each bone forming the joint so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. In certain implementations, cutting instrument 10 is used prepare the ends of one or both bone faces in addition to or in lieu of using a different cutting instrument. Such utilization of cutting instrument 10 can be in addition to or in lieu of cutting soft tissue as described herein.

Independent of the type of tissue removing instrument used, the tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against a guide surface (e.g., between a slot defined between two guide surfaces) of the bone preparation guide to guide the cutting instrument for bone removal.

After realignment (or in lieu of a separate realignment step), the clinician may or may not compress one or more bone faces of the opposed bone portions together (e.g., the end faces of the proximal and distal portions of the first metatarsal, the end faces of the first metatarsal and medial cuneiform). The clinician may compress the end faces together with hand pressure and/or using a compressing instrument physically attached to both the first bone portion and the second bone portion.

After suitably realigning at least a portion of the first metatarsal, the technique of FIG. 8 involves fixating the moved position (810). In some examples, a provisional fixation step is performed in which one or more temporary fixation pins are deployed to hold the moved position of the metatarsal (e.g., by inserting the fixation pin through the moved metatarsal or portion thereof and into one or more adjacent bones). A permanent fixation device can be applied across the joint separating the prepared bone ends to hold a moved position of a bone for subsequent fusion. For example, one or more permanent fixation devices can be applied across the joint (osteotomy) formed by cutting the first metatarsal into the distal metatarsal portion and the proximal metatarsal portion. As another example, one or more permanent fixation devices can be applied across the first TMT joint 126 separating the first metatarsal from the medial cuneiform. Example permanent fixation devices include, but are not limited to, pins (e.g., intramedullary nail, K-wire, Steinmann pin), plates, screws, staples, and combinations thereof. With time and healing, the realigned bone can subsequently fuse to the end face of the opposed bone to provide a fused joint.

Various examples have been described. These and other examples are within the scope of the following claims.

The invention claimed is:

1. A method of releasing a first metatarsal for realignment, the method comprising:

surgically accessing a sesamoidal ligament in a foot of a patient;

advancing a guiding projection of a cutting instrument under the sesamoidal ligament, thereby capturing the sesamoidal ligament between the guiding projection of the cutting instrument and a cutting surface of the cutting instrument recessed relative to a distal end of the guiding projection; and subsequently cutting the sesamoidal ligament with the cutting surface of the cutting instrument.

2. The method of claim 1, wherein advancing the guiding projection of the cutting instrument under the sesamoidal ligament comprises advancing the cutting instrument in distal to proximal direction in an intermetatarsal space separating a first metatarsal from a second metatarsal.

3. The method of claim 1, wherein advancing the guiding projection of the cutting instrument under the sesamoidal ligament comprises pushing the cutting instrument in a first direction, and subsequently cutting the sesamoidal ligament with the cutting surface comprises further pushing the cutting instrument in the first direction.

4. The method of claim 1, wherein:

advancing the guiding projection of the cutting instrument under the sesamoidal ligament comprises advancing the guiding projection of the cutting instrument under an accessory supervisory ligament; and subsequently cutting the sesamoidal ligament with the cutting surface of the cutting instrument comprises cutting the accessory supervisory ligament.

5. The method of claim 4, further comprising advancing the guiding projection of the cutting instrument under a proper collateral ligament, and subsequently cutting the proper collateral ligament.

6. The method of claim 4, further comprising:

advancing the guiding projection of the cutting instrument under at least one of a lateral sesamoid phalangeal ligament, a lateral metatarsophalangeal ligament, an adductor tendon, and a deep transverse metatarsal ligament; and cutting the at least one of the lateral sesamoid phalangeal ligament, the lateral metatarsophalangeal ligament, the adductor tendon, and the deep transverse metatarsal ligament with the cutting surface of the cutting instrument.

7. The method of claim 1, wherein advancing the guiding projection of the cutting instrument under the sesamoidal ligament comprises advancing the guiding projection of the cutting instrument between the sesamoidal ligament and a surface of at least one of a first metatarsal and a proximal phalanx.

8. The method of claim 1, wherein surgically accessing the sesamoidal ligament comprises cutting into a first metatarsophalangeal joint capsule.

9. The method of claim 8, wherein cutting into the first metatarsophalangeal joint capsule comprises cutting into a lateral side of the first metatarsophalangeal joint capsule from a dorsal side of the foot.

10. The method of claim 1, wherein the cutting surface defines a cutting edge, and a distal-most edge of the cutting surface is spaced a distance from the distal end of the guiding projection a distance within a range from 5 mm to 15 mm.

11. The method of claim 1, wherein:

the cutting instrument comprises a cutting head defining the cutting surface and the guiding projection;

the cutting head defines a length extending from the distal end to a proximal end, and a width perpendicular to the length, the width extending from a first side edge of the cutting head to a second side edge of the cutting head; and the guiding projection forms the second side edge of the cutting head.

12. The method of claim 11, wherein:

the guiding projection comprises a first guiding projection and a second guiding projection;

the first guiding projection forms the first side edge of the cutting head; and the second guiding projection forms the second side edge of the cutting head.

13. The method of claim 1, wherein the guiding projection defines a cylindrical cross-sectional shape along at least a portion of its length.

14. The method of claim 1, wherein the distal end of the guiding projection is blunt, and the guiding projection comprises a tapers down to the blunt distal end.

15. The method of claim 1, wherein the cutting instrument comprises a cutting head defining the cutting surface and the guiding projection, the cutting head defines a thickness, and the thickness of the cutting head tapers across the cutting surface.

16. The method of claim 15, wherein the thickness of the cutting head tapers across the cutting surface at a taper angle within a range from 5 degrees to 25 degrees.

17. A method of realigning at least a portion of a first metatarsal, the method comprising:

surgically accessing a sesamoidal ligament in a foot of a patient;

advancing a guiding projection of a cutting instrument under the sesamoidal ligament, thereby capturing the sesamoidal ligament between the guiding projection of the cutting instrument and a cutting surface of the cutting instrument recessed relative to a distal end of the guide projection, and subsequently cutting the sesamoidal ligament with the cutting surface of the cutting instrument;

moving at least a portion of a first metatarsal in at least one plane; and fixating a moved position of the portion of the first metatarsal by applying at least one bone fixation device.

18. The method of claim 17, wherein moving at least the portion of the first metatarsal in at least one plane comprises moving an entire length of the first metatarsal in at least one plane, and further comprising:

surgically accessing a tarsometatarsal joint separating the first metatarsal from a medial cuneiform in the foot of the patient;

preparing an end of the first metatarsal; and preparing an end of the medial cuneiform.

19. The method of claim 17, further comprising cutting the first metatarsal into a distal portion and a proximal portion, wherein moving at least the portion of the first metatarsal in at least one plane comprises moving the distal portion of the first metatarsal relative to the proximal portion.

20. The method of claim 17, wherein the at least one plane comprises a frontal plane.

21. The method of claim 17, wherein advancing the guiding projection of the cutting instrument under the sesamoidal ligament comprises advancing the guiding projection of the cutting instrument under an accessory supervisory ligament; and subsequently cutting the sesamoidal ligament with the cutting surface of the cutting instrument comprises cutting the accessory supervisory ligament.

22. The method of claim 21, further comprising advancing the guiding projection of the cutting instrument under a proper collateral ligament, and subsequently cutting the proper collateral ligament.

23. The method of claim 21, further comprising:

advancing the guiding projection of the cutting instrument under at least one of a lateral sesamoid phalangeal ligament, a lateral metatarsophalangeal ligament, an adductor tendon, and a deep transverse metatarsal ligament; and cutting the at least one of the lateral sesamoid phalangeal ligament, the lateral metatarsophalangeal ligament, the adductor tendon, and the deep transverse metatarsal ligament with the cutting surface of the cutting instrument.

24. The method of claim 17, wherein surgically accessing the sesamoidal ligament comprises cutting into a lateral side of a first metatarsophalangeal joint capsule.

* * * * *